US011117976B2

(12) United States Patent
Braciale et al.

(10) Patent No.: US 11,117,976 B2
(45) Date of Patent: Sep. 14, 2021

(54) COMPOSITIONS AND METHODS FOR REGULATING ERYTHROPOIESIS

(71) Applicant: University of Virginia Patent Foundation, Charlottesville, VA (US)

(72) Inventors: Thomas J. Braciale, Charlottesville, VA (US); Taeg S. Kim, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 16/139,428

(22) Filed: Sep. 24, 2018

(65) Prior Publication Data
US 2019/0071515 A1 Mar. 7, 2019

Related U.S. Application Data

(63) Continuation of application No. 14/651,708, filed as application No. PCT/US2013/074245 on Dec. 11, 2013, now abandoned.

(60) Provisional application No. 61/736,246, filed on Dec. 12, 2012.

(51) Int. Cl.
*A61K 39/00* (2006.01)
*A61K 38/18* (2006.01)
*A61K 38/19* (2006.01)
*A61K 38/20* (2006.01)
*C07K 16/28* (2006.01)
*A61K 39/395* (2006.01)
*A61K 45/06* (2006.01)
*A61K 38/00* (2006.01)

(52) U.S. Cl.
CPC ...... *C07K 16/2896* (2013.01); *A61K 39/3955* (2013.01); *A61K 45/06* (2013.01); *A61K 38/00* (2013.01); *A61K 2039/505* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,703,008 A | 10/1987 | Lin | |
| 4,816,567 A | 3/1989 | Cabilly et al. | |
| 4,946,778 A | 8/1990 | Ladner et al. | |
| 4,975,369 A | 12/1990 | Beavers et al. | |
| 4,987,121 A | 1/1991 | Baertschi et al. | |
| 5,001,065 A | 3/1991 | Larrick et al. | |
| 5,075,431 A | 12/1991 | Shively et al. | |
| 5,081,235 A | 1/1992 | Shively et al. | |
| 5,169,939 A | 12/1992 | Gefter et al. | |
| 5,202,238 A | 4/1993 | Fell, Jr. et al. | |
| 5,204,244 A | 4/1993 | Fell et al. | |
| 5,231,026 A | 7/1993 | Chang | |
| 5,292,867 A | 3/1994 | Chang | |
| 5,354,847 A | 10/1994 | Liu et al. | |
| 5,436,157 A | 7/1995 | Herr et al. | |
| 5,472,693 A | 12/1995 | Gourlie et al. | |
| 5,482,856 A | 1/1996 | Fell, Jr. et al. | |
| 5,491,088 A | 2/1996 | Hellstrom et al. | |
| 5,500,362 A | 3/1996 | Robinson et al. | |
| 5,502,167 A | 3/1996 | Waldmann et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,644,003 A | 7/1997 | Arai et al. | |
| 5,661,016 A | 8/1997 | Lonberg et al. | |
| 5,804,177 A | 9/1998 | Humphries | |
| 5,831,012 A | 11/1998 | Nilsson et al. | |
| 6,510,495 B1 | 1/2003 | Nobukiyo | |
| 6,994,982 B1 | 2/2006 | Watt et al. | |
| 2003/0022244 A1 | 1/2003 | Solomon et al. | |
| 2003/0095966 A1* | 5/2003 | Liu | A61K 39/0008 424/144.1 |
| 2004/0047862 A1* | 3/2004 | Lazarus | C07K 16/283 424/144.1 |
| 2005/0287580 A1 | 12/2005 | Watt et al. | |

(Continued)

FOREIGN PATENT DOCUMENTS

| | | |
|---|---|---|
| EP | 2931293 B1 | 2/2019 |
| WO | WO 2006/091535 | 8/2006 |
| WO | WO 2009/063461 A1 | 5/2009 |

OTHER PUBLICATIONS

Meletis et al. Correction of anaemia and thrombocytopenia in a case of adult Type I osteopetrosis with recombinant human erythropoietin (rHuEPO). British Journal of Haematology, vol. 89:911-913 (1995). (Year: 1995).*

Tokuriki et al. Stability effects of mutations and protein evolvability; Current Opinion in Structural Biology, 19:596-604 (2009). (Year: 2009).*

Song et al. Monoclonal IgG can ameliorate immune thrombocytopenia in a murine model of ITP: an alternative to to IVIG. Blood vol. 101/9:3708-3713 (May 2003). (Year: 2003).*

Lloyd et al. Modelling the human immune response: performance of a 1011 human antibody repertoire against a broad panel of therapeutically relevant antigens. Protein Engineering, Design & Selection 2009, vol. 22/No. 3:159-168 (2009). (Year: 2009).*

Thomas et al., e pub. Aug. 27, 2012, Cancer Research, CD24 is an effector of HIF-1 driven primary tumor growth and metastasis.

(Continued)

*Primary Examiner* — Elizabeth C. Kemmerer
*Assistant Examiner* — Regina M DeBerry
(74) *Attorney, Agent, or Firm* — Jenkins, Wilson, Taylor & Hunt, P.A.

(57) ABSTRACT

The present application discloses a previously unknown function of CD24 expressed on a subset of dendritic cells. The invention encompasses regulating CD24 on these cells to regulate erythropoiesis, induce EPO production and levels, increase RBC levels, and to treat, for example, stress-mediated erythropoiesis. The compositions and methods of the invention are useful, for example, in treating anemia.

32 Claims, 25 Drawing Sheets
(25 of 25 Drawing Sheet(s) Filed in Color)
Specification includes a Sequence Listing.

(56) References Cited

U.S. PATENT DOCUMENTS

| | | | |
|---|---|---|---|
| 2007/0185017 A1* | 8/2007 | Aggarwal | C07K 14/47 514/1.7 |
| 2007/0264277 A1 | 11/2007 | Behrens et al. | |
| 2010/0166649 A1* | 7/2010 | Shin | A61K 49/0008 424/1.11 |
| 2011/0003387 A1 | 1/2011 | Abbot et al. | |
| 2011/0123483 A1* | 5/2011 | Roth | A61K 31/7088 424/85.1 |
| 2015/0285802 A1* | 10/2015 | Polyak | G01N 33/57415 435/6.12 |
| 2015/0329639 A1 | 11/2015 | Braciale et al. | |

OTHER PUBLICATIONS

Zhou, et al., "CD24 is a genetic modifier for risk and progression of multple sclerosis," PNAS, vol. 100, No. 25, pp. 15041-15046 (2003).

Jaggupilli, et al., "Significance of CD44 and CD24 as Cancer Stem Cell Markers: an Enduring Ambiguity," Clinical and Developmental Immunology, vol. 2012, Article ID 708036, pp. 1-11.

Wu et al., "Antibody-Directed Lentiviral Gene Transduction for Live-Cell Monitoring and Selection of Human iPS and hES Cells," PLos ONE, vol. 7, Issue 4 pp. 1-10 (2012).

Kume et al., "Long-term tracking of murine hematopoietic cells transduced with a bicistronic retrovirus containing CD24 and EGFP genes," Gene Therapy vol. 7, pp. 1193-1199 (2000).

Cao et al., "Upregulation of VEGF-A and CD24 Gene Expression by the tGLI1 Transcription Factor Contributes to the Aggressive Behavior or Breast Cancel Cells," Oncogene, vol. 31, No. 1 pp. 104-115 (2012).

Zhu et al., "Identification of Glycoprotein Markers for Pancreatic Cancer CD24+CD44+ Stem-like Cells Using Nano-LC-MS/MS and Tissue Microarray," J. Proteome Research, vol. 11, pp. 2272- 2281 (2012).

Fang et al., "CD24: from A to Z, Cellular & Molecular Immunology," vol. 7, pp. 100-103 (2010).

Salamone, et al., "Antibodies recognising CD24 LAP epitope on human T cells enhance CD28 and IL-2 T cell proliferation," J. of Leukocyte Biology, vol. 69, pp. 215-223 (2001).

Hunte et al., Acquisition of CD 24 expression by Lin-CD43+ B220(low)ckit(hi) cells coincide with commitment to the B cell lineage. Eur J. Immunol. vol. 28, No. 11, pp. 3850-3856 (1998).

Wilson et al., Subpopulations of mature murine thymocytes: properties of CD4-CD8+ and CD4+CD8-thymocytes lacking the heat-stable antigen. Cell Immunol vol. 117, No. 2, pp. 312-326 (1998).

Alterman et al., Characterization of the murine heat-stable antigen: an hematolymphoid differentiation antigen defined by the J11d. M1/69 and B2A2 antibodies. Eur J. Immunol, vol. 20, No. 7, pp. 1597-1602 (1990).

Springer et al., "Monoclonal xenogeneic antibodies to murine cell surface antigens: identification of novel leukocyte differentiation antigens," Eur J Immunol. vol. 8, No. 8 pp. 539-551, (1978).

Fischer, et al., "Signal Transcution in Lymphotic and Myleoid Cells via CDE 24, A New Member of Phosphoinositol-Anchored Membrane Molecules," Journal of Immunology, vol. 144, No. 2 pp. 638-641 (1990).

Williams et al., "Indentification of a novel dendritic cell surface antigen defined by carbohydrate specific CD24 antibody cross-reactivity," Immunology, vol. 89 pp. 120-125 (1996).

Kay, et al., "CD24, A signal Transducer Modulating B Cell Activation Responses is a Very Shprt Peptide with a Glycosyl Phosphatidylinositol Membrane Anchor," J. Immunology, vol. 147, No. 4 pp. 1412-1416 (1991).

Altschul et al. "Basic Local Alignment Search Tool," J. Mol. Biol., vol. 215, pp. 403-410 (1990).

Altschul et al. "Gapped BLAST and PSI-BLAST: a new generation of protein database search programs," Nucleic Acids Res., vol. 25, No. 17, pp. 3389-3402 (1997).

Altschul et al. "Protein database searches for multiple alignments," Proc. Natl. Acad. Sci. USA, vol. 87, No. 14, pp. 5509-5513 (1990).

Barbas III, "Synthetic human antibodies," Nature Medicine, vol. 1, pp. 837-839 (1995).

Barr et al. "Reverse Two-hybrid Screening Identifies Residues of JNK Required for Interaction with the Kinase Interaction Motif of JNK-interacting Protein-1," J. Biol. Chern., vol. 279, No. 41, pp. 43178-43189 (2004).

Baumann et al. "CD24 interacts with and promotes the activity of c-src within lipid rafts in breast cancer cells, thereby increasing integrin-dependent adhesion," Cellular and Molecular Life Sciences, vol. 69, No. 3, pp. 435-448 (2012).

Chen et al., "CD24 and Siglec-10 Selectively Repress Tissue Damage-Induced Immune Responses," Author Manuscript, pp. 1-12, 2009; Published in final edited form as: Science, vol. 323, pp. 1722-1725 (2009).

Chevray et al. "Protein interaction cloning in yeast: Identification of mammalian proteins that react with the leucine zipper of Jun," Proc. Natl. Acad. Sci. USA, vol. 89, pp. 5789-5793 (1992).

Chien et al. "The two-hybrid system: A method to identify and clone genes for proteins that interact with a protein of interest," Proc. Natl. Acad. Sci. USA, vol. 88, pp. 9578-9582 (1991).

Chou et al. "Prediction of β-Turns," Biophys. J., vol. 26, pp. 367-383 (1979).

Cote et al. "Generation of human monoclonal antibodies reactive with cellular antigens," Proc. Natl. Acad. Sci. USA, vol. 80, No. 7, pp. 2026-2030 (1983).

Decision to Grant corresponding to European Application No. 13862444.0 dated Jan. 24, 2019.

Devereux et al. "A comprehensive set of sequence analysis programs for the VAX," Nucl. Acids Res., vol. 12, No. 1, pp. 387-395 (1984).

Extended European Search Report corresponding to European Application No. 13862444.0 dated Jul. 29, 2016.

Fasbender et al. "Complexes of Adenovirus with Polycationic Polymers and Cationic Lipids Increase the Efficiency of Gene Transfer in Vitro and in Vivo,", J. Biol. Chem., vol. 272, No. 10, pp. 6479-6489 (1997).

Gait, Oligonucleotide Synthesis. A Practical Approach, Febs Letters, vol. 188, No. 1, pp. 166-167 (1985).

Hardy et al., "Resolution and Characterization of Pro-B and Pre-Pro-B Cell Stages in Normal Mouse Bone Marrow," J. Exp. Med., vol. 173, pp. 1213-1225 (1991).

Hunt "Hematopoietic Effects of PhotoFrin," The University of British Columbia, Canada, PhD Thesis, pp. 1-55 (1996).

Intent to Grant corresponding to European Application No. 13862444.0 dated Oct. 2018.

International Search Report corresponding to International Application No. PCT/US2013/074245 dated Apr. 15, 2014.

IPRP and Written Opinion corresponding to International Application No. PCT/US2013/074245 dated Jun. 16, 2015.

Jones et al. "Replacing the complementarity-determining regions in a human antibody with those from a mouse," Nature, vol. 321, pp. 522-525 (1986).

Karlin et al. "Applications and statistics for multiple high-scoring segments in molecular sequences," Proc. Natl. Acad. Sei. USA, vol. 90, pp. 5873-5877 (1993).

Karlin et al. "Methods for assessing the statistical significance of molecular sequence features by using general scoring schemes," Proc. Natl. Acad. Sci. USA, vol. 87, pp. 2264-2268 (1990).

Kim et al., "Stress-associated erythropoiesis initiation is regulated by type 1 conventional dendritic cells," Journal of Clinical Investigation, vol. 125, No. 10, pp. 3965-3980 (2015).

Kohler et al. Continuous cultures of fused cells secreting antibody of predefined specificity, Nature, vol. 256, pp. 495-497(1975).

Kyte et al. "A Simple Method for Displaying the Hydropathic Character of a Protein," J. Mol. Biol., vol. 157, pp. 105-132 (1982).

Lato et al. "In vitro selection of RNA lectins: using combinatorial chemistry to interpret ribozyme evolution," Chem. Biol., vol. 2, No. 5, pp. 291-303 (1995).

Li et al. "High Level Desmin Expression Depends on a Muscle-specific Enhancer," J. Bio. Chem., vol. 266, No. 10, pp. 6562-6570 (1991).

(56) References Cited

OTHER PUBLICATIONS

Lonberg et al. "Antigen-specific human antibodies from mice comprising four distinct genetic modifications," Nature, vol. 368, pp. 856-859 (1994).
Miyake et al. "Purification of human erythropoietin," J. Biol. Chem., vol. 252, pp. 5558-5564 (1977).
Morrison et al. "Chimeric human antibody molecules: Mouse antigen-binding domains with human constant region domains," Proc. Natl. Acad. Sci. USA, vol. 81, pp. 6851-6855 (1984).
Morrison, "Success in specification," Nature, vol. 368, pp. 812-813 (1994).
Neuberger, "Generating high-avidity human Mabs in mice," Nature Biotechnology, vol. 14, p. 826 (1996).
Nielsen et al. "Altered Erythrocytes and a Leaky Block in B-Cell Development in CD24/HSA-Deficient Mice," Blood, vol. 89, No. 3, pp. 1058-1067 (1997).
Notice of Publication corresponding to European Application No. 13862444.0 dated Sep. 23, 2015.
Office Action corresponding to European Application No. 13862444.0 dated Aug. 28, 2015.
Office Action corresponding to European Application No. 13862444.0 dated Aug. 17, 2016.
Office Action corresponding to European Application No. 13862444.0 dated Sep. 22, 2017.
Office Action corresponding to European Application No. 13862444.0 dated Mar. 22, 2018.
Office Action corresponding to U.S. Appl. No. 14/651,708 dated Aug. 24, 2016.
Office Action corresponding to U.S. Appl. No. 14/651,708 dated Nov. 14, 2016.
Office Action corresponding to U.S. Appl. No. 14/651,708 dated Mar. 22, 2018.
Office Action corresponding to U.S. Appl. No. 14/651,708 dated Aug. 9, 2017.
Orlandi et al. "Cloning immunoglobulin variable domains for expression by the polymerase chain reaction," Proc. Natl. Acad. Sci. USA, vol. 86, No. 10, pp. 3833-3837 (1989).
Pillai et al., "Differential expression of a surface antigen recognized by a monoclonal antibody, J11 d, on unprimed and primed B cells," J. Immunology, vol. 137, No. 3, pp. 791-797 (1986).
Redmond et al. "Kruppel-like Factor 2 Regulated Gene Expression in Mouse Embryonic Yolk Sac Erythroid Cells," Author Manuscript, pp. 1-23 (2012) [Published in final edited form as: Blood Cells, Moleculesand Diseases, vol. 47, No. 1, pp. 1-11 (2011)].
Ribeil et al. "Hsp70 regulates erythropoiesis by preventing caspase-3-mediated cleavage of GATA-1," Nature, vol. 445, No. 7123, pp. 102-105 (2007).
Schabath et al. "CD24 affects CXCR4 function in pre-B lymphocytes and breast carcinoma cells," Journal of Cell Science, vol. 119, No. 2, pp. 314-325 (2006).
Shirasawa et al. "Gene Expression of CD24 Core Peptide Molecule in Developing Brain and Developing Non-Neural Tissues," Developmental Dynamics, vol. 198, pp. 1-13 (1993) (Year: 1993).
Symington et al., "Hematopoietic Subpopulations Express Cross-Reactive, Lineage-Specific Molecules Detected by Monoclonal Antibody," Molecular Immunology, vol. 21, No. 6, pp. 507-514, 1984.
Tuszynski et al. "Thrombospondin Promotes Platelet Aggregation," Blood, vol. 72, No. 1, pp. 109-115 (1988).
Wallis et al. "A novel RNA motif for neomycin recognition," Chem. Biol., vol. 2, Iss. 8, pp. 543-552 (1995).
Wells, "Additivity of Mutational Effects in Proteins," Biochemistry, vol. 29, No. 37, pp. 8509-8517 (1990).
Winter et al. "Man-made antibodies," Nature, vol. 349, pp. 293-299 (1991).
Yutzey et al. "An Internal Regulatory Element Controls Troponin I Gene Expression," Mol. Cell. Bio., vol. 9, No. 4, pp. 1397-1405 (1989).
Hunt et al. "Monoclonal Antibody LR-1 Recognizes Murine Heat-Stable Antigen, a Marker of Antigen-Presenting Cells and Developing Hematopoietic Cells," International Archives of Allergy and Immunology, vol. 111, pp. 218-229 (1996).
Hunt et al. "The Porphyrin Photosensitizer Photofrin® Elevates Murine Splenic Erythropoiesis," Immunopharmacology and Immunotoxicology, vol. 20, No. 3, pp. 409-420 (1998).
Ngo et al. "Computational Complexity, Protein Structure Prediction, and the Levinthal Paradox," The Protein Folding Problem and Tertiary Structure Prediction, edited by Merz et al., pp. 433-440 and 492-495 (1994).

* cited by examiner

COMPOSITIONS AND METHODS FOR REGULATING ERYTHROPOIESIS

CROSS REFERENCE TO RELATED APPLICATIONS

This application is a continuation application of U.S. application Ser. No. 14/651,708, filed Jun. 12, 2015, which is a national stage filing of International Application No. PCT/US2013/074245, filed Dec. 11, 2013, which claims priority under 35 U.S.C. § 119(e) to U.S. Provisional Application Ser. No. 61/736,246 filed Dec. 12, 2012, the disclosures of which are incorporated by reference in their entirety herein.

STATEMENT REGARDING FEDERALLY SPONSORED RESEARCH OR DEVELOPMENT

This invention was made with government support under Grant Nos. AI015608, AI083024, and HL033391, awarded by The National Institutes of Health. The government has certain rights in the invention.

BACKGROUND

Anemia is defined as a diminished number of red blood cells (RBC) or less than the normal quantity of hemoglobin in the blood, and is the single-most common hematological disorder. Because hemoglobin (found inside RBCs) normally carries oxygen from the lungs to the tissues, anemia leads to hypoxia (lack of oxygen) in organs. Since all human cells depend on oxygen for survival, varying degrees of anemia can have a wide range of clinical consequences. People with anemia don't get enough oxygen-rich blood and they may feel tired or experience shortness of breath during routine activities. With severe or long-lasting anemia, the lack of oxygen in the blood can damage the heart, brain, and other organs and may even cause death. The NIH's National Heart Lung and Blood Institute has identified 3 major causes of anemia: acute or chronic blood loss (e.g., hemorrhage or vascular leak), excessive blood cell destruction (hemolysis) or deficient red blood cell production (ineffective hematopoiesis). Anemia is a common complication of cancer and frequently occurs following chemotherapy treatment for cancer. Anemia is also common in patients undergoing dialysis, acute severe inflammation such as sepsis, individuals with rheumatologic disorders, other chronic infectious or inflammatory diseases, and, importantly, among the elderly. The incidence of anemia increases with age.

Erythropoiesis, the production of erythrocytes, occurs continuously in vivo to offset the turnover (decrease) of erythrocytes in circulation (~120 days of lifespan in adults). This process is a tightly regulated physiological mechanism to ensure an adequate supply of erythrocytes to deliver oxygen to tissues. Erythropoietin (EPO), a glycoprotein hormone with a potent stimulatory ability for RBC production, is produced in the kidney. Under basal/homeostatic conditions, EPO stimulates the division and differentiation of committed erythroid progenitors into mature erythrocytes primarily in the bone marrow (and to a lesser extent in the spleen). EPO production and release into the circulation is augmented in response to hypoxia with concomitant accelerated production of the erythrocytes. This stress-induced generation of erythrocytes occurs both in the bone marrow and importantly in "extramedullary hematopoiesis sites" notably the spleen and to a lesser extent, the liver. A loss of kidney function as is seen in chronic renal failure (CRF), for example, typically results in decreased production of EPO and a concomitant reduction in red blood cells.

Maintenance of an adequate supply of oxygen to the body tissues is vital to survival. In the United States alone, several million people suffer from anemia secondary to renal failure, chronic inflammatory disease and malignancies (U.S. Pat. No. 4,987,121, hereby incorporated by reference in its entirety). Since to a large degree the oxygen-carrying capacity of blood is governed by the concentration of erythrocytes in the blood, the appropriate regulation of erythropoiesis is also crucial.

Human urinary EPO was purified by Miyake et al. (J. Biol. Chem. 252, 5558 (1977)) from patients with aplastic anemia. However, the amount of purified EPO protein obtained from this source was insufficient for therapeutic applications. The identification and cloning of the gene encoding human EPO and expression of recombinant protein was disclosed in U.S. Pat. No. 4,703,008 to Lin, the disclosure of which is incorporated herein by reference.

Cell adhesion proteins are dynamic molecules involved in several aspects of cellular function including migration, inflammation, and tissue development. For example, the maturation of hematopoietic cells is associated with the regulated expression of numerous genes, some of which encode cell surface proteins that mediate maturation-stage-specific signals into and out of the cell. This is accomplished by binding of the cell surface protein to a variety of ligands such as soluble interleukins and adhesion receptors either on other cells or within the extracellular matrix. One such cell adhesion molecule found in most cells of hematopoietic lineages is CD24, a glycoprotein consisting of 31 to 35 amino acid residues anchored to the plasma membrane by glycosyl phosphatidylinositol (Kay et al., J. Immunol., 1991, 147, 1412-1416).

CD24, also known as Heat Stable Antigen (HSA), is a glycoprotein expressed at the surface of many cell types including dendritic cells (DCs). DCs perform many critical roles of immune system regulation. CD24 has been described, inter alia, in B-cell development and B-cell neoplasia, in the developing pancreas and brain, and in regenerating muscle, keratinocytes, renal tubules, and a large variety of malignant tumors There is a long felt need in the art for compositions and methods useful for stimulating erythropoiesis. The present application satisfies these needs.

SUMMARY OF THE INVENTION

Disclosed herein is the discovery of a previously unknown function of CD24 expressed by a distinct subset of splenic and bone marrow (BM) dendritic cells; that is, engagement of CD24 on this spleen (or bone marrow) resident cell type results in the stimulation of erythropoietin (EPO) production and concomitant vigorous production of red blood cells (RBCs/erythrocytes) in the spleen and bone marrow of treated mice. The current invention provides a novel strategy to enhance stress-mediated erythropoiesis or stimulate erythropoiesis.

Further disclosed herein is the unexpected resulted that engagement of the CD24 on this subset of splenic (or bone marrow) dendritic cells activate the cells to in turn enhance the activity of erythrocytic stem cell precursors in the spleen/BM and to promote endogenous EPO production. This invention has significant therapeutic potential in the treatment of diseases and disorders of RBC levels, particularly acute and chronic anemia, because of its ability to target the stimulation, activation, and proliferation of erythroid progenitors in the spleen/BM as its primary effect as well as to enhance the production of endogenous EPO and to augment the potency of EPO administered therapeutically to subjects suffering from chronic anemia without endogenous EPO stores.

It is also disclosed herein that treatment of mice with an anti-CD24 antibody stimulates an increase in circulating endogenous EPO levels in the blood, with a prior/concomitant rapid expansion of erythroid progenitors and a concomitant dramatic increase in reticulocytes (immature RBCs).

One key advantage of the compositions and methods of the present invention is to activate and to expand the numbers of early erythroid progenitors, the induction of long-term production of endogenous erythropoietin in the body compared to other therapies requiring repetitive injections of exogenous recombinant erythropoietin. Another important advantage is the use of the strategy to augment the effect of recombinant EPO administered therapeutically to treat anemia.

Because the invention is based, at least in part, on the discovery disclosed herein that certain DC cells are a target for stimulating erythropoiesis, the invention provides compositions and methods for targeting those cells and for increasing the numbers of the cells or of active cells. This includes stimulating proliferation to increase the numbers as well as methods for obtaining and administering cells to a subject in need thereof.

The present invention is related to a method of simulating stress-induced erythropoiesis in mammals. In one embodiment, the method mimics the body's response to stresses causing acute or chronic hypoxia such as hemorrhage or anemia. Identified herein are agents, for example, a unique monoclonal antibody directed to CD24, which in part through their action on CD24 displayed by a specific subset of splenic (or bone marrow) DC dramatically enhances both EPO production and extramedullary hematopoiesis.

In one embodiment, the method of the invention provides for administration of at least one agonist of CD24 activity. The method comprises administering to a subject a pharmaceutical composition comprising a pharmaceutically-acceptable carrier, an effective amount of at least one agonist of CD24, and optionally at least one additional therapeutic agent. In one aspect, the method stimulates CD24 expressed on dendritic cells. In one aspect, the dendritic cells in the mouse express the cell surface molecule CD8α and in the human the cell surface molecule BDCA3/CD141. In one aspect, the agonist for CD24 on this subset of dendritic cells is a small molecule, drug, prodrug, or an antibody, or a biologically active fragment or homolog thereof, directed against CD24. In one aspect, the antibody is a monoclonal antibody. In another aspect, the invention provides for stimulating the CD24 receptor on a distinct subset of splenic (or bone marrow) dendritic cells with at least one agonist directed to CD24 other than an agonistic antibody directed against CD24. One of skill in the art will appreciate that other agonists can be used as well, such as other antibodies, other proteins or peptides that bind with CD24 or activate it, small molecules, drugs, or prodrugs. Optionally, additional therapeutic agents can be administered, including, but not limited to, anti-inflammatory agents, G-CSF, IL-4, SCF, Flt3L, EPO, BMP4, anti-microbial agents, and host-derived danger associated-pattern molecules.

One of ordinary skill in the art will appreciate that any agent stimulating CD24 or its signaling pathway on the same cells is also encompassed by the present invention, including, but not limited to drugs and other peptides or ligands of CD24.

In one aspect, an agonist of the invention, or other compounds with similar agonist activity for CD24, may be administrated to an individual to increase erythropoiesis through its effect on endogenous EPO/G-CSF/SCF and splenic erythroid precursors. An agonist of the invention also has the potential to be used as an adjuvant to enhance the effect of recombinant EPO used in the treatment of chronic anemia. An increase in erythropoiesis can be determined, for example, by measuring the concentration of EPO in the serum and by measuring the hemoglobin or reticulocyte/erythrocyte levels in the blood of the recipients before and after treatment with the agent which activates CD24.

In one embodiment, the present invention provides compositions and methods useful for enhancing the activity of erythrocytic stem cell precursors and promoting the production of erythrocytes and erythroid progenitor cells. In one aspect, the method is useful for promoting stress erythropoiesis and treating conditions responding to hypoxic stress. In another aspect, the method is useful for enhancing the activity of erythrocytic stem cell precursors in the spleen and promoting the production of erythrocytes and erythroid progenitor cells.

In one aspect, the method comprises administering to a subject in need thereof a pharmaceutical composition comprising an effective amount of an agonist of CD24 on a distinct subset of splenic, kidney, or bone marrow dendritic cells, a pharmaceutically-acceptable carrier, and optionally at least one additional therapeutic agent. In one aspect, the erythroid progenitor cells are basophilic erythroblasts in the spleen. In another aspect, the erythroid progenitor cells are polychromatophilic erythroblasts in the spleen. In another aspect, the erythroid progenitor cells are orthochromatic erythroblasts in the spleen. In one embodiment, the distinct subset of splenic dendritic cells is the BDCA3/CD141 dendritic cell subset in humans.

An agonist of CD24 can be any type of compound that activates CD24 as disclosed herein or that stimulates CD24 activity. An agonist of CD24 activity includes compounds such as drugs or proteins that act either upstream or downstream of CD24. In one embodiment, the agonist is an antibody. In one aspect, the antibody is a single chain antibody, a monoclonal antibody, F(ab)2 fragments of a monoclonal antibody, a bi-specific antibody, a chimeric antibody, a synthetic antibody, a polyclonal antibody, or a humanized antibody, or active fragments or homologs thereof. In one aspect, the antibody is human. In one aspect, the monoclonal antibody is M1/69 (IgG2b), 91 (IgG2a), 30-F1 (IgG2c), J11d (IgM), eBioSN3, or ML5, or biologically active fragments or homologs thereof. Recombinant monoclonal antibodies (mAb) are playing an increasing role in the management of many diseases including malignancies, inflammatory bowel disease, rheumatoid arthritis, and asthma.

In one embodiment, an antibody of the invention is directed against CD24 having the amino acid sequence of SEQ ID NO:2 (human CD24) or SEQ ID NO:4, or homologs or fragments thereof.

In one aspect, a monoclonal antibody is directed against CD24. In one aspect, the antibody is an F(ab)2 fragment of a monoclonal antibody (mAb) to CD24. In one aspect, the CD24 is human CD24.

Therefore, the present invention further encompasses development of additional anti-human CD24 specific agonist monoclonal antibodies and humanized monoclonal anti-human CD24 antibodies for use in the invention. The antibody(s), or biologically active fragments or homologs thereof, can be subjected to preclinical testing, for example in vitro with human or animal cells or in animal models, as well as clinical testing. The invention also encompasses the identification and development of other compounds which mimic the agonist effect of anti-CD24 monoclonal antibodies on erythropoiesis induced by CD24 engagement such as the natural ligand for CD24 or derivatives thereof and small molecules with this CD24-dependent signaling stimulatory capacity.

Methods for preparing antibodies are described herein (see Embodiments and Examples) and are known in the art, including isolation and identification of single chain molecules produced by techniques such as phage or yeast display.

In one embodiment, the present invention provides compositions and methods for stimulating erythropoiesis. In one aspect, the stimulation is via a CD24 regulatory pathway. In one aspect, the present invention provides administering a pharmaceutical composition comprising a therapeutically effective amount of a compound of the invention to a subject in need thereof. In one aspect, the compound stimulates CD24 or an upstream or downstream component of the CD24 signal transduction pathway. In one aspect, a compound of the invention directly interacts with CD24. In another aspect, a compound stimulates an event or molecule upstream from CD24. In one aspect, a compound of the invention stimulates a downstream event in the CD24 signal transduction pathway. In one aspect, CD24 is stimulated using a drug, agent, antibody, homolog, derivative, or fragment thereof, or other compound or molecule that elicits the same effect on CD24 disclosed herein and stimulates erythropoiesis as described herein. In one aspect, the antibody is a monoclonal antibody, or biologically active derivative, homolog, or fragment thereof. In one aspect, a monoclonal agonistic antibody binds to CD24 and stimulates CD24-dependent cellular signaling events, resulting in the production of erythropoietin, G-CSF, SCF, expansion of erythroid progenitors and generation of red blood cells. In one aspect, the present invention provides a method of increasing erythroid progenitors.

In one aspect, an advantage of the present invention over previous methods of inducing erythropoiesis or stimulating erythropoietin production and levels is that the present method directly enhances the activity and stimulates the production of early erythroid progenitors. Another advantage is that the present method can be performed without multiple or repetitive injections of exogenous EPO. A third advantage is that the present method can be used as a combination therapy in conjunction with EPO administration.

In one embodiment the present invention provides compositions and methods for treating a disease, disorder, or condition associated with a decrease in erythrocyte production. The method comprises administering to a subject a pharmaceutical composition comprising a pharmaceutically-acceptable carrier, an effective amount of at least one agonist of CD24, and optionally at least one additional therapeutic agent. In one aspect, the method stimulates CD24 expressed on dendritic cells. In one aspect, the method the dendritic cells express the cell surface molecule BDCA3/CD141. In one aspect, the agonist is a small molecule, drug, prodrug, or an antibody, or a biologically active fragment or homolog thereof, directed against CD24.

The present application discloses the unexpected result that CD24 and its signal transduction pathway can be regulated to stimulate, inter alia, erythropoiesis. To that end, the present invention encompasses the use of or the targeting of nucleic acids and proteins and various homologues, derivatives, and fragments thereof. In one aspect, the homologues, derivatives, and fragments have the same activity as the complete or mature sequence. In one aspect, the have the function or activity based on the context in which they are used or described.

The present invention further encompasses compositions and methods to induce the CD24 signal transduction pathway and to increase CD24 expression and levels. One of ordinary skill in the art will appreciate that any ligand or molecule which is an agonist of CD24 can be used. In one aspect, an expression vector comprising a nucleic acid sequence encoding the CD24 protein, or a biologically active fragment or homolog thereof can be used and a cell of interest can be targeted or a transfected cell can be administered to a subject.

Various antibodies directed against CD24, or biologically active derivatives, homologs, or fragments of the antibodies, are encompassed by the methods of the invention. Human CD24 has the amino acid sequence of SEQ ID NO:2 and mouse CD24 has the amino acid sequence of SEQ ID NO:4. These antibodies directed against the CD24 sequences include, but are not limited to, monoclonal antibodies, polyclonal antibodies, and humanized antibodies. The antibodies may be directed against or made against appropriate fragments or homologs of CD24. The methods of the invention also encompass the identification and development of other compounds which mimic the effect of anti-CD24 monoclonal antibodies on erythropoiesis induced by CD24 engagement, such as the natural ligand(s) for CD24 or derivatives thereof and small molecules with this CD24 receptor stimulatory capacity.

In one aspect, the increase in number of erythroid progenitors, reticulocytes, or erythrocytes following treatment with a CD24 agonist is from at least about 5, 10, 15, 20, 25, 30, 35, 40, 45, 50, 55, 60, 65, 75, or 100%. In one aspect, the increase in cell numbers is at least 2 fold. In one aspect, the increase is at least 5 fold. In one aspect, the increase is at least 10 fold. Disclosed herein are the results of studies elucidating the mechanism for the observed erythropoiesis and demonstrating the relative safety of administering an anti-CD24 antibody in mice. Additional studies have verified the safety of the method (data not shown).

In one aspect, the present invention provides for the use of an agonist of CD24 to stimulate an increase in SCF, G-CSF, and EPO levels. In one aspect, SCF levels are increased. In one aspect, EPO levels are increased. In one aspect, G-CSF levels are increased. In one aspect, two of the three increase and in another aspect, all three increase. In one aspect, the agonist is an antibody directed against CD24. The present invention provides compositions and methods for stimulating an increase in EPO levels and in reticulocyte levels through a CD24 pathway. In one aspect, the invention also provides for increasing the numbers of the DC subset described herein, including stimulation of the cells to proliferate or administering exogenous cells. In one aspect, the compositions and methods are useful for increasing c-Kit expressing erythroid progenitors. In one aspect, SCF and G-CSF are increased by stimulating CD24 on the target DCs of the invention. In one aspect, the increase in SCF is cell surface SCF, and SCF and G-CSF are secreted by the target DCs.

In one aspect, the increase in SCF levels following treatment with a CD24 agonist is from at least about 5, 10, 15, 20, 25, 30, 35, 40, 45, 50, 55, 60, 65, 75, or 100%.

In one aspect, the increase in EPO levels following treatment with a CD24 agonist is from at least about 5, 10, 15, 20, 25, 30, 35, 40, 45, 50, 55, 60, 65, 75, or 100%.

In one aspect, the increase in G-CSF levels following treatment with a CD24 agonist is from at least about 5, 10, 15, 20, 25, 30, 35, 40, 45, 50, 55, 60, 65, 75, or 100%.

Other compounds can be administered in conjunction with the agonist of CD24 to augment various aspects of erythropoiesis. These compounds include, but are not limited to, GM-CSF, IL-4, SCF, Flt3L, EPO, and BMP4. Other compounds that can be used in combination with agonists of the invention include host-derived danger associated-pattern molecules (HMGB1, Hsp70, etc.). Other therapeutic agents (antibiotics, anti-inflammatories, etc.) and drugs can also be administered in conjunction with the agonist therapy of the invention.

In one embodiment, blocking agents of CD24 can be administered prior to treatment with the agonist of CD24. For example, recombinant human CD24 fused to an immunoglobulin molecule could be administered.

In one embodiment, the present invention provides compositions and methods useful for treating anemia. In one aspect, the anemia comprises aplastic anemia. In another aspect, the anemia comprises hypoplastic anemia. In one aspect, the present invention provides contacting an erythroid progenitor cells with a compound of the invention in an amount effective to augment erythropoiesis. In one aspect, the anemia is associated with chronic renal failure. In one aspect, the anemia is associated with end-stage renal disease. In another aspect, the anemia is associated with transplantation. In one aspect, the transplantation is renal transplantation. In another aspect, the anemia is associated with cancer. In one aspect, the anemia is associated with acquired immune deficiency syndrome. In another aspect, the anemia is associated with chemotherapy. In one aspect, the anemia is associated with radiotherapy. In another aspect, the anemia is associated with bone marrow transplantation. In another aspect, the anemia is acute and associated with sepsis. In one aspect, the anemia is sickle cell anemia. In another aspect the anemia is associated with rheumatoid arthritis, chronic persistent infection such as HIV, tuberculosis, hepatitis B and C, and chronic, and chronic anemia in the elderly (not treated by iron replacement and/or nutritional supplementation). In one aspect, the disease, disorder, or condition is anemia.

A dosage regimen for augmenting erythropoiesis with the active agents is based on a variety of factors, including the type of injury, the age, weight, sex, medical condition of the individual, the severity of the condition, the route of administration, and the particular compound employed. Thus, the dosage regimen may vary, but can be determined routinely by a physician using standard methods.

In one aspect, an antibody of the invention can be administered at a dose of about 0.1 mg/kg to about 100 mg/kg body weight. In another aspect, an antibody of the invention can be administered at a dose of about 1.0 mg/kg to about 50 mg/kg. In yet another aspect, an antibody of the invention can be administered at a dose of about 5.0 mg/kg to about 25 mg/kg body weight. In another aspect, an antibody of the invention can be administered at a dose of about 1.0, 1.5, 2.0, 2.5, 3.0, 3.5, 4.0, 4.5, 5,0, 5,5, 6.0, 6,5, 7.0, 7.5, 8,0, 8.5, 9.0, 9,5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, and 20.0 mg/kg body weight. The invention further encompasses similar increments within each range of doses described herein. In one embodiment, the agonist or additional therapeutic agent is administered at a dose of about 1 µg/kg body weight to about 1 g/kg body weight.

The present invention encompasses administering an agonist of the invention more than once to a subject. In one aspect, a composition comprising at least one agonist of the invention is administered at least twice. In another aspect, a composition is administered at least five times. In yet another aspect, a composition is administered at least 10 times. In one aspect, a composition of the invention is administered at least once per day. In another aspect, a composition is administered at least once per week. In yet another aspect, a composition is administered at least twice per week. In another aspect, a composition is administered at least once per month. In yet another aspect, a composition is administered at least twice per month.

In one aspect, after administration of the agonist to the subject, a second round of the agonist is administered to stimulate a second wave of production of erythrocytes and erythroid progenitor cells. In one aspect, a subject may receive three or more rounds of treatment with the agonist, in another aspect five or more rounds, in yet another aspect, 10 or more rounds, and in a further aspect, 25 or more rounds. In one aspect, the total number of doses can be from about 2 to about 100; about 5 to about 75; about 10 to about 50 times; and about 20 to about 40.

The invention further encompasses the use of unit doses, for example unit doses of about 0.01, 0.05, 0.1, 0.5, 0.75, 1.0, 1.25, 1.5, 1.75, 2.0, 5.0, 10, 15, 20, 25, 30, 50, or 100 grams.

The treatment regimen will vary depending on the disease being treated, based on a variety of factors, including the type of injury, the age, weight, sex, medical condition of the individual, the severity of the condition, the route of administration, and the particular compound employed. The treatment can include administration of a pharmaceutical composition of the invention once or more than once. Other therapeutic drugs and agents can be administered as well. Agents which stimulate erythropoietin, SCF and G-CSF can also be administered.

In another embodiment, erythropoiesis is augmented ex vivo by obtaining a sample of bone marrow cells, as is known in the art, potentiating erythropoietin-induced differentiation with at least one active agent of the invention and infusing the treated cells back into a subject in need thereof. The methods also encompass the use of the subset of DC cells of the invention disclosed herein.

The full-length peptide of (80 amino acid residues in humans; SEQ ID NO:2) comprises a putative signal peptide (amino acid residues 1-26) and a mature peptide of 54 amino acid residues (amino acid residues 27-80 of the full-length peptide).

Useful full-length sequences of the invention include, but are not limited to, human and mouse nucleic acid and amino acid sequences for CD24.

Those four CD24 sequences (SEQ ID NOs: 1-4) are as follows:

human nucleic acid; GenBank accession no. NM_013230.2; (2194 bp; mRNA)-

SEQ ID NO: 1
gggtctcgccggctcgccgcgctccccaccttgcctgcgcccgcccggag ccagcggttctccaagcacccagcatcctgctagacgcgccgcgcaccga cggaggggacatgggcagagcaatggtggccaggctcgggctggggctgc tgctgctggcactgctcctacccacgcagatttattccagtgaaacaaca actggaacttcaagtaactcctcccagagtacttccaactctgggttggc cccaaatccaactaatgccaccaccaaggcggctggtggtgccctgcagt caacagccagtctcttcgtggtctcactctctcttctgcatctctactct taagagactcaggccaagaaacgtcttctaaatttccccatcttctaaac ccaatccaaatggcgtctggaagtccaatgtggcaaggaaaaacaggtct tcatcgaatctactaattccacaccttttattgacacagaaaatgttgag aatcccaaatttgattgatttgaagaacatgtgagaggtttgactagatg atggatgccaatattaaatctgctggagtttcatgtacaagatgaaggag aggcaacatccaaaatagttaagacatgatttccttgaatgtggcttgag aaatatggacacttaatactaccttgaaaataagaatagaaataaaggat gggattgtggaatggagattcagttttcatttggttcattaattctataa ggccataaaacaggtaatataaaaagcttccatgattctattttatatgta catgagaaggaacttccaggtgttactgtaattcctcaacgtattgtttc gacagcactaatttaatgccgatatactctagatgaagttttacattgtt gagctattgctgttctcttgggaactgaactcactttcctcctgaggctt tggatttgacattgcatttgacctttttatgtagtaattgacatgtgccag ggcaatgatgaatgagaatctaccccccagatccaagcatcctgagcaact cttgattatccatattgagtcaaatggtaggcatttcctatcacctgttt ccattcaacaagagcactacattcatttagctaaacggattccaaagagt agaattgcattgaccacgactaatttcaaaatgcttttttattattattat ttttttagacagtctcactttgtcgcccaggccggagtgcagtggtgcgat ctcagatcagtgtaccatttgcctcccgggctcaagcgattctcctgcct cagcctcccaagtagctgggattacaggcacctgccaccatgcccggcta atttttgtaattttagtagagacagggtttcaccatgttgcccaggctgg tttcgaactcctgacctcaggtgatccacccgcctcggcctcccaaagtg ctgggattacaggcttgagcccccgcgcccagccatcaaaatgctttttta tttctgcatatgttgaatacttttttacaatttaaaaaaatgatctgttttt gaaggcaaaattgcaaatcttgaaattaagaaggcaaaaatgtaaaggag tcaaaactataaatcaagtatttgggaagtgaagactggaagctaatttg cattaaaattcacaaacttttatactctttctgtatatacattattttctt taaaaaacaactatggatcagaatagccacatttagaacacttttttgtta tcagtcaatattttttagatagttagaacctggtcctaagcctaaaagtgg gcttgattctgcagtaaatcttttacaactgcctcgacacacataaacct tttttaaaaatagacactccccgaagtcttttgttcgcatggtcacacact gatgcttagatgttccagtaatctaatatggcacagtagtcttgatgac caaagtccttatttccatctttagaaaactacatgggaacaaacagatcg aacagttttgaagctactgtgtgtgtgaatgaacactcttgctttattcc agaatgctacatctattttggattgtatattgtgtttgtgtatttacg ctttgattcatagtaacttcttatggaattgatttgcattgaacacaaac tgtaaataaaaagaaatggctgaaagagcaaaaaaaaaaaa human amino acid; GenBank Accession No. ACI46150.1; (80 amino acids)-

SEQ ID NO: 2

MetGlyArgAlaMetValAlaArgLeuGlyLeuGlyLeuLeuLeuLeu

AlaLeuLeuLeuProThrGlnIleTyrSerSerGluThrThrThrGly

ThrSerSerAsnSerSerGlnSerThrSerAsnSerGlyLeuAlaPro

AsnProThrAsnAlaThrThrLysAlaAlaGlyGlyAlaLeuGlnSer

ThrAlaSerLeuPheValValSerLeuSerLeuLeuHisLeuTyrSer (single letter sequence of:

mgramvarlglglllllalllptqiyssetttgtssnssqstsnsglapnp tnattkaaggalqstaslfvvslsllhlys)

-mouse nucleic acid; GenBank Accession No. NM_009846; (1825 bp; mRNA)-

SEQ ID NO: 3 ccaccttgcctgcgcccgcgcgagcttagcagatctccacttaccgaaca tctagagagtcgcgccgcgcgccgacggagcggacatgggcagagcgatg gtggccaggctagggctgggttgctgcttctggcactgctcctacccac gcagatttactgcaaccaaacatctgttgcaccgtttcccggtaaccaga atatttctgcttccccaaatccaagtaacgctaccaccagaggggtggc agctccctgcagtccacagctggtctcctggctctctctctctctcttct acatctctactgttagagactcaggccaggaaacgtctctacttccccat cttctacacctaccccaaatggcaaccacaagtccaatgtgatcaggaag aaacaggtccacctcgaattggctgttaccatatctcaacagaaaacacg gagaattcgaaattcgacgggattaaaggacgcgtgaaaggtttgagaga agagagatgccgctattgaatctgctggagttttacatcccaagatgaag acagcattcagaattgatgtgatttccttgaatgtggcttaggaaatgtg gacacttaaaactctcacttgaaattgggcacaggtttgatgtagagata aggacggggtgcggaatggagacccattttgtcattgattcatctgaccg ataaggccatagtgcagttaggtgatattcgaaagcttctttgatgctct ttatgtatatgttggaaggaactaccaggcgttgctttaaattcccaatg tgttgtttcgttactactaatttaataccgtaagctctaggtaaagttcc atgttgttgaactctgactgttctctttggaattgaacgttttgcatcct cctcctgtggcttaggtctgacattgtatttgaccttttactagtaatta acatgtgccaggcaatggtggattggaacccatccccaagtccagccacc actgaataaatctgatttcaaaagtcaaacagtagacatttcccattgtc gtttctcactcaccacaagcaccaaattcactagagtacactggttccag agagcagaatcatgttggccttggctaatttcaaaatgctgtcttttact ttggtatatgttgagggcttttcataatttaaagtgtgttctgttagcaa ggcaaaaattatgagtcttaattctacaggcaaatatgcaaaggagccaa aactgtaaacccagcatttgggatgtgaagactggaagctaactctcatt gaattcacaaagtcattatacaaatttctgtacatacttatttttttttaa gagaaaaacaaacggtggatcagaatagccacgtttggaatactttggtt atccattcatattttagatagttattggtcctgtgcctgaaaggggggct -continued
tggttctaccgtaagttttccaatttccttgatatacacataccttcta aaacctagacatttcctgaaaaaaatcttttgttcgcatggtcacacact gatgcttacccgtacagtagtcttgataaccagagtcattttctccatct ttagaaaccttcctgggaagaaggagagctcacagacccgaagctactgt gtgtgtgaatgaacactccccttgcctcacacctgaatgctgtacatcta tttgattgtaaattgtgtttgtgtatttatgctttgattcatagtaactt ctcatgttatggaattgatttgcattgaacacaaactgtaaataaaagaa agaaatggcggagaaaaaaaaaa mouse amino acid; GenBank Accession No. NP_033976;
(76 amino acids)-
SEQ ID NO: 4
MetGlyArgAlaMetValAlaArgLeuGlyLeuGlyLeuLeuLeuLeu AlaLeuLeuLeuProThrGlnIleTyrCysAsnGlnThrSerValAla ProPheProGlyAsnGlnAsnIleSerAlaSerProAsnProSerAsn AlaThrThrArgGlyGlyGlySerSerLeuGlnSerThrAlaGlyLeu LeuAlaLeuSerLeuSerLeuLeuHisLeuTyrCys (single letter sequence of:

mgramvarlglglllllalllptqiycnqtsvapfpgnqnisaspnpsnat trgggsslqstagllalslsllhlyc)

The invention further provides for the use of the proteins or peptides where one or more conservative amino acid substitutions are made in the sequence and that the substitution has no effect on the desired biological activity, where such activity is desired. In one aspect, one conservative amino acid substitution is made. In one aspect, at least two conservative amino acid substitutions are made. When two or more substitutions are made, they do not have to be at adjacent amino acid residue positions.

In one aspect, an antibody or other agonist of CD24 activity that stimulates erythropoiesis, SCF, or EPO can be identified using methods and assays described herein and the identified agents can be used to practice the methods of the invention. The invention therefore provides methods for identifying agents useful to practice the invention and provides for the use thereof.

The invention also encompasses the identification and development of other compounds (drugs, peptides, ligands, etc.) which mimic the agonist effect of anti-CD24 monoclonal antibody on erythropoiesis induced by CD24 engagement such as the natural ligand for CD24 or derivatives thereof and small molecules with this CD24-dependent signaling stimulatory capacity. The examples provide assays for screening for the activity of such agents that activate CD24, particularly in the dendritic cell populations used herein.

In one embodiment, the present invention provides a method of identifying of an agonist of CD24 useful for stimulating erythropoiesis wherein a dendritic cell expressing CD24 is contacted with a test compound, the stem cell factor level is measured in the cell following the contact, and an increase in stem cell factor in the cell relative to a control cell not contacted with the test compound, is an indication that the test compound is an agonist of CD24. The stem cell factor level can also be compared to a standard and to cells treated with a compound that does not stimulate stem cell factor or erythropoiesis, even if the compound interacts with CD24 or binds to CD24. In one aspect, the test compound is an antibody directed against CD24. In one aspect, the test compound interacts with CD24. In one aspect, CD24 protein levels are measured. In another aspect, CD24 messenger RNA levels are measured.

According to the present invention, potential therapeutic agents may be screened for the ability to stimulate splenic erythrocyte progenitor (CD45−/+c-Kit+Ter119− and/or Ter119+CD45−) expansion in the spleen following administration of the agents to mice.

Alternatively, potential therapeutic agents may be screened for the ability to increase the expression level of the murine stem cell factor (mSCF) on the splenic CD8α+ DC subset following treating the isolated conventional dendritic cells with candidate compounds. In one aspect, agents are screened for the ability to increase the expression level of the mSCF on the splenic CD8α-CD11b+ DC subset following treating the isolated conventional dendritic cells.

In addition, potential therapeutic compounds/agonists may be screened for the ability to increase the expression level of the human stem cell factor (hSCF) on human dendritic cells expressing the cell surface molecule BDCA3/CD141.

Controls can include antibodies that are directed against CD24 but do not stimulate erythropoiesis or SCF (see examples).

In a further aspect, the present invention provides kits with components for promoting erythropoiesis, wherein the kits comprise an effective amount of at least one active agent to stimulate CD24 or the CD24 pathway of the invention, and instructions for using the active agent as a therapeutic. In one embodiment, the kit further comprises a pharmaceutically acceptable carrier, such as those adjuvants described above. In another embodiment, the kit further comprises a means for delivery of the active agent to a mammal. Such devices include, but are not limited to matrical or micellar solutions, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. Optionally, at least one additional therapeutic agent can be administered and can be provided in the kit. In a further embodiment, the kits also comprise an amount of erythropoietin effective to accelerate erythropoiesis.

As disclosed herein, a kit comprising agonists of the invention is useful for, inter alia, treating anemia, stimulating erythropoiesis, stimulating CD24-mediated stress erythropoiesis, stimulating extramedullary erythropoiesis, stimulating SCF, stimulating EPO, stimulating G-CSF, stimulating erythroid progenitor proliferation, and increasing the number of erythrocytes, reticulocytes, and erythroid progenitor cells.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Mice were infused intraperitoneally (i.p.) with 150 μg control rat IgG or αCD24 (clone M1/69) and necropsied on days 1, 3 or 5 after Ab treatment. (A) Representative macroscopic appearance of the spleens over time after αCD24 mAb infusion in wt B6 mice (n>20). (B) M1/69 treatment promotes stress erythropoiesis. Single cell suspensions prepared from spleens at d5 post treatment were analyzed for cell types expressed by flow cytometry and enumerated (n>5): leukocyte (CD45$^+$Ter119$^-$, group I); erythrocytes (CD45$^+$Ter119$^+$, group II), and erythroid progenitor cells (CD45$^-$ Ter119$^+$, group III). (C) We further examined for the erythroid compartment, based on the differential expression of Ter119 and the transferrin receptor, CD71. Erythroblast subsets, consisting of basophilic (Ter119$^+$CD71$^{hi}$, group I—least mature), polychromatophilic (Ter119$^+$CD71$^{med}$, group ii), and orthochromatic (Ter119$^+$CD71$^{lo}$, group iii) erythroblasts in spleen. (D) Erythropoiesis induced by M1/69 treatment requires CD24 expression. To investigate if these effects are specific to M1/69 mAb interaction with CD24, mice deficient in CD24 expression were given Ig or αCD24 mAb and examined at d5 p.t. for gross appearance of spleens shown in (D) and absolute number of CD45$^-$Ter119$^+$ (data not shown, n=3–5). (E) CD24 expression by the cells of hematopoietic origin, but not the cells in stromal compartment, is required for M1/69-induced stress erythropoiesis. To assess the contribution of CD24-expressing cell type from the respective compartment, BM chimeric mice were established by transferring 2×10$^6$ donor BM cells derived from either WT or CD24$^{-/-}$ mice into lethally irradiated either WT or CD24$^{-/-}$ recipient mice. At 6 weeks after BM cell reconstitution, these chimeric mice were infused with Ig or M1/69. At d5, mice were necropsied and evaluated for gross appearance of spleens (right panel) and for erythroid progenitor cells frequency/numbers (left panel) (n=3/group). CD24 expression on cells of bone marrow/hematopoietic origin was necessary and sufficient for stress-induced hematopoiesis mediated by M1/69 treatment. It is also noteworthy that erythropoiesis induced by αCD24 mAb depends on F(ab)$_2$, but not Fc, fragments (data not shown). Data represent mean±SD. ***P<0.001.

Figure 2B:
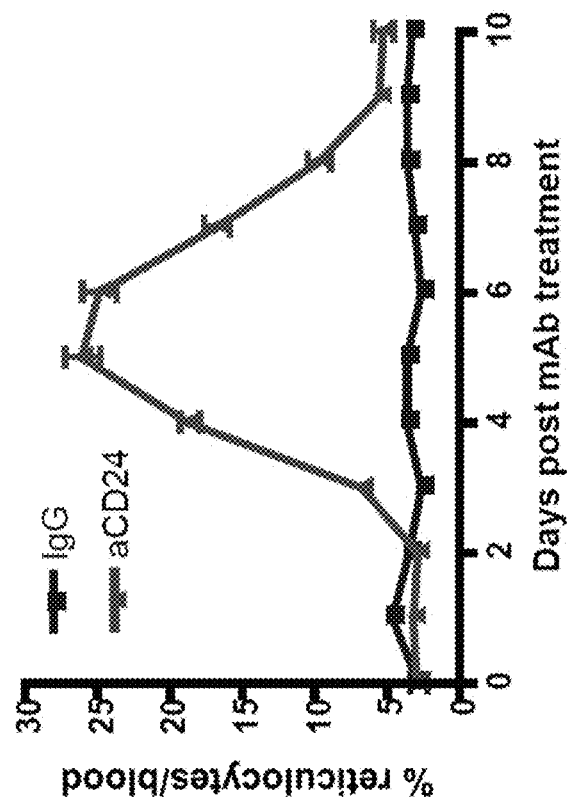
Figure 2A:
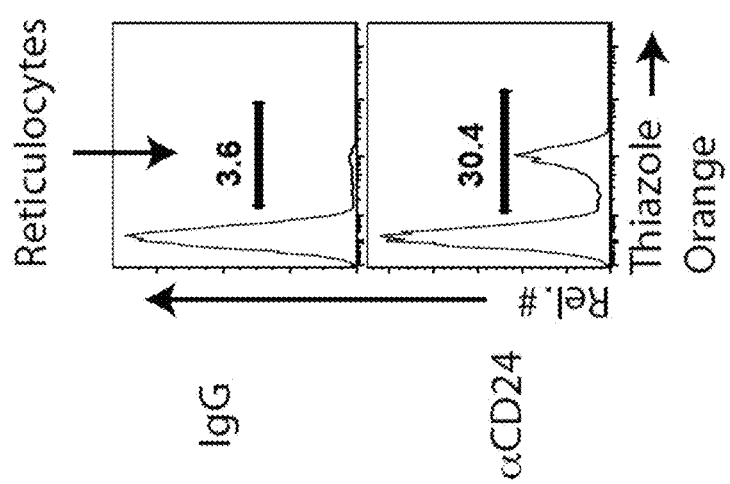
Figure 3B:
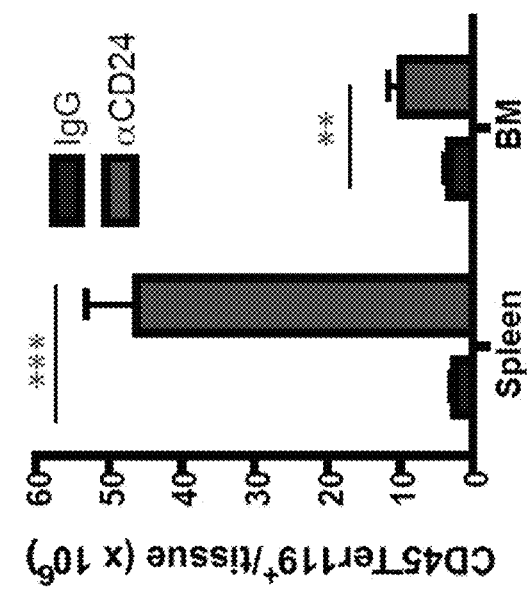
Figure 3A:
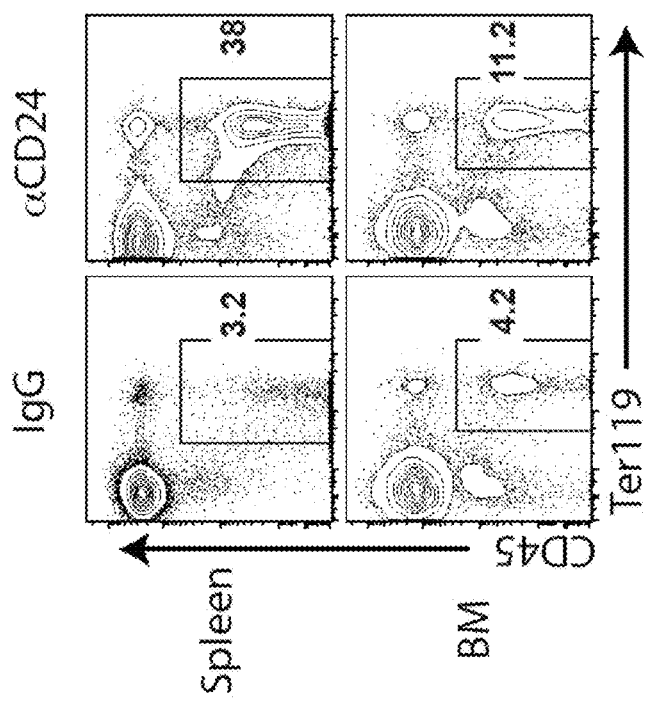
Figure 3D:
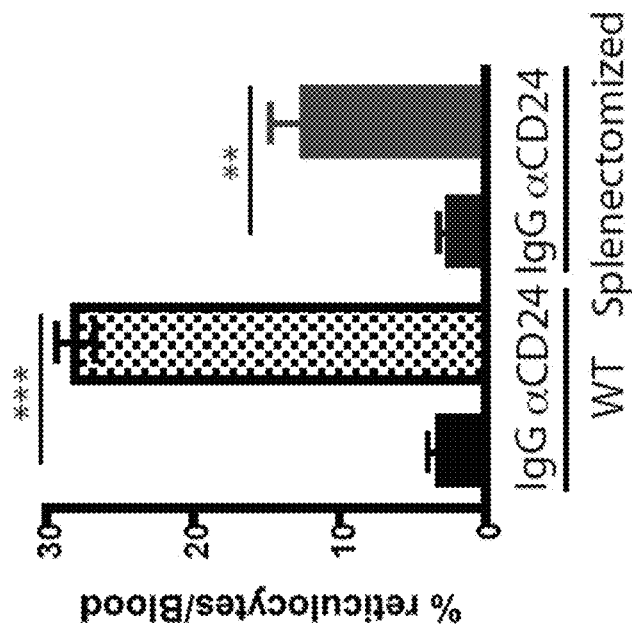
Figure 3C:
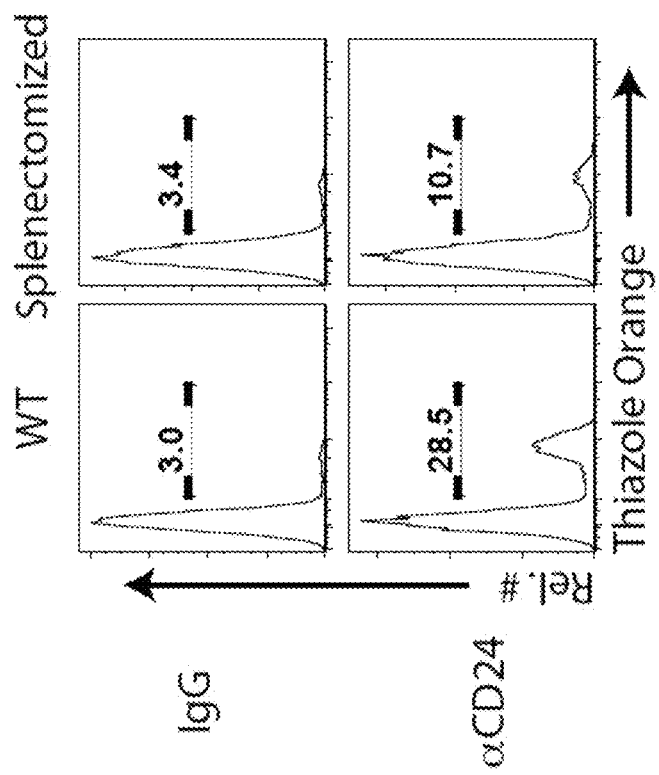
Figure 3E:
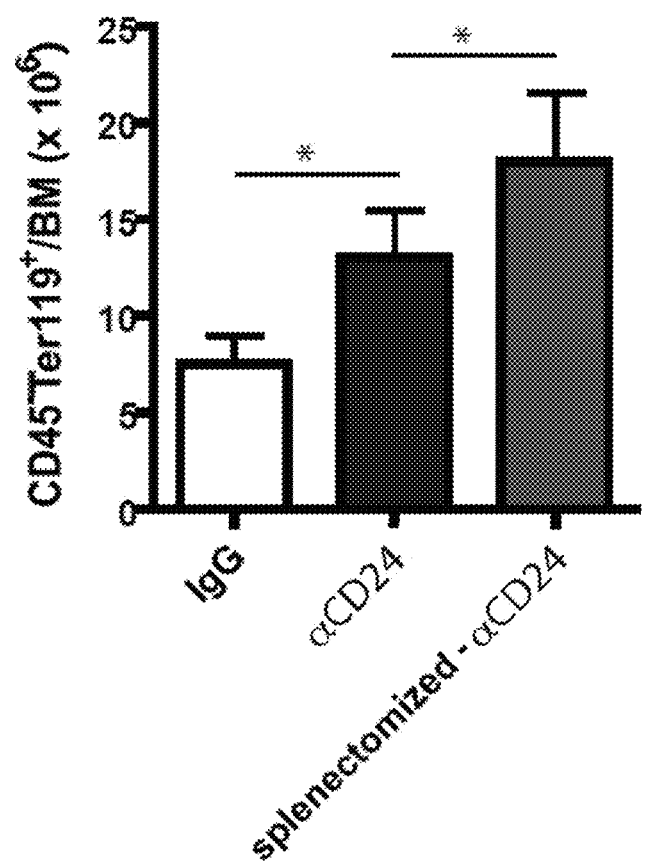

FIG. 2, comprising FIGS. 2A to 2B. Stress erythropoiesis in the peripheral blood after αCD24 mAb treatment. The effect of M1/69 treatment in erythropoiesis was also observed in peripheral blood. WT mice were infused i.p. with 150 µg control Ig or αCD24 and examined at the indicated time points. Peripheral blood smears were prepared at d5 p.t. and stained by methylene blue. Typical staining of residual RNA in reticulocytes—immature RBC for about a day in the blood stream before developing into mature RBCs—is examined by microscope (data now shown). (A) Percentages of reticulocytes in the peripheral blood were also assessed by flow cytometry using thiazole orange staining (to selectively stain nucleic acid, in this case RNA) for about an 1 hr at room temperature. A representative flow cytometric analysis of examining reticulocytes in blood at d5 is shown. Data are representative of >20 independently repeated experiments. Numbers denote the percentage of reticulocytes staining with thiazole orange dye in peripheral blood. (B) Kinetic analyses of percent reticulocytes circulating in the blood of mice treated with Ig or αCD24 at the indicated dates (n=4-7/day).

FIG. 3, comprising FIGS. 3A to 3E. Stress erythropoiesis induced by αCD24 mAb treatment depends on the spleen and, to a lesser extent, bone marrow. To study the extent of CD24-induced erythropoiesis in the spleen as well as BM, respectively, WT mice were injected i.p. with 150 µg control Ig or αCD24. (A) Representative of the frequency of CD45$^-$Ter119$^+$ erythroid progenitors in spleens (top panels in A) and BM (bottom panels in A), as measured by flow cytometry at d5 after αCD24 treatment. (B) Total erythroid progenitors per spleen and BM, respectively, at d5 are depicted (n=3-5). (C-E) To evaluate the impact of spleen on stress erythropoiesis, mice were splenectomized prior to antibody administration. WT B6 mice that had undergone splenectomy 5 weeks earlier were treated as in A. At d5, percentage of reticulocytes in the blood (C and D) and absolute cell number of CD45$^-$Ter119$^+$ cells in BM (E) was assessed by flow cytometric analyses (n=3-5). Mean±SD is shown (*P<0.001, P<0.01 and **P <0.05).

FIG. 4, comprising FIGS. 4A to 4F. A novel role of conventional dendritic cells, in particular CD8α+ DC, in CD24-mediated stress erythropoiesis in vivo. To investigate the specific cell type(s) governing stress erythropoiesis in vivo, we employed mice deficient in or depleted of various cell types (T, B, and inflammatory monocytes, neutrophils and NK cells). Our analyses found that none of these hematopoietic cell lineages were important regulators of stress erythropoiesis induced by M1/69 treatment (data not shown). Next, we assessed the impact of dendritic cells (DCs) on the stress erythropoiesis. DCs are well recognized as professional antigen presenting cells, composed of heterogeneous subpopulations. In lymphoid organs such as spleens, three major subsets of DCs are classified; two conventional DC (cDC) subsets including CD8α$^+$CD11b$^-$ (CD8α$^+$ cDC, group I) and CD8α$^-$CD11b$^+$ (CD11b$^+$ cDC, group II) (top panels in A) and plasmacytoid DC (pDC) (data not shown). Notably, it is the CD8α$^+$ cDC among DC subsets in the spleen which express cell surface CD24 at the highest level (lower panel in A). To study the role of CD24$^{hi}$ CD8α$^+$ cDC in αCD24 mAb-induced stress erythropoiesis, we obtained mice lacking transcriptional factor Batf3 gene (Batf3 KO mice), which are developmentally devoid of CD8α$^+$ cDC in the spleen and of nodes and a related lineage of DC which populate certain non-lymphoid tissues such as lung and kidney etc. (B). WT and Batf3 KO mice were injected i.p. with 150 µg control Ig or αCD24. After 5 days, gross appearance of spleens (data not shown), a representative of the percentage of circulating reticulocytes in the blood (C) and absolute number of CD45$^-$Ter119+ erythroid progenitors in the spleens (D) were assessed by flow cytometry (n=4-6). The results of these analyses indicate that CD8α$^+$ cDC in the spleen and possibly a related tissue-specific DC subset play a critical role in promoting stress erythropoiesis. To exclude a possibility of an additional unanticipated role of the Batf3 gene on erythropoiesis, i.e., other than its role in the generation of a specific DC lineage, we employed CD11c-DTR mice, which are engineered to express non-human primate diphtheria toxin receptor (DTR) driven off of murine CD11c (a conventional marker for murine DC) promoter. Upon diphtheria toxin (DTx) administration (100 ng/mouse via i.p.), DTR expressing CD11c+ cells (that is cDC) are conditionally selectively ablated within 24 hrs (E). These cDC-ablated mice were infused with Ig or αCD24 mAb 1 day after first DTx administration. With second dose of DTx at d1 post treatment, mice were necropsied at d5 for gross appearance of the spleens (data not shown). The percentage of circulating reticulocytes in the blood (data not shown) and absolute number of CD45$^-$Ter119$^+$ erythroid progenitors in the spleens (F) were assessed by flow cytometry (n=3-5). The analysis demonstrates that CD11c$^+$ cells, i.e., cDC, play a critical role in regulating the development of stress hematopoiesis mediated by CD 24 engagement. Data represent mean±SD.

FIG. 5, comprising FIGS. 5A to 5D. Conventional DCs are required for the expansion of c-Kit expressing erythroid progenitors in the spleen during extramedullary stress erythropoiesis. Recent studies show that stress erythropoiesis depends on a population of stress erythroid progenitor cells that are distinct from the counterpart present in BM. The development, expansion, and differentiation of these progenitors are regulated in part by a complex of less understood signals. We initially attempted to identify these progenitors based on c-Kit (CD117) expression as engagement of this receptor has been demonstrated to be essential for stress erythropoiesis. (A-C) WT mice were injected i.p. with 150 μg control Ig or αCD24. (A) Anti-CD24 mAb treatment promotes the expansion of cKit$^+$CD45$^{+/-}$ cells in the spleen. At d3 and 5 post treatments, single cells suspensions prepared from the necropsied spleens were stained with fluorochrome-conjugated mAb recognizing c-Kit (left panel). In contrast to Ig treated mice, mice undergoing M1/69 treatment have a dramatic increase in the number of c-Kit$^+$ cells, peaking at d3 (n>6), with little to no expression of the standard hematopoietic lineage marker CD45 (i.e., CD45$^{+/-}$ c-Kit+cells (right panel). (B) CD45$^{+/-}$c-Kit$^+$ progenitors exhibited greater (compared to DC and B cells) forward (FSC) and side scatter (SSC) plot by flow cytometry analyses and expressed different levels of Ter119 as well as CD71, indicative of progenitor cells with erythroid lineage commitment such as proerythroblasts. (C) To determine if c-Kit$^+$ proerythroblasts undergo proliferative expansion, the M1/69-treated mice were fed with nucleic acid analog, BrdU, at d5 to label proliferating cells. After 24 hr BrdU injection, c-Kit$^+$ erythroid progenitors were examined for active uptake of BrdU in combination with staining for a proliferation-associated nuclear antigen, Ki-67. In contrast to c-Kit$^+$ cells in the Ig-treated spleen, c-Kit$^+$ erythroid progenitors isolated from the mice treated with M1/69 underwent active proliferation. (D) Furthermore, in support of the importance of splenic cDC in orchestrating stress erythropoiesis, ablation of cDC by treatment of CD11c-DTR mice with diphtheria toxin resulted in minimal expansion of these progenitors when stimulated by αCD24 mAb infusion (n=3-5). Collectively, our data strongly support the view that cDCs, particularly lymph node-resident CD8α+ cDC subset and/or a developmentally related tissue-resident cDC subset, play an essential role in regulating extramedullary stress erythropoiesis.

FIG. 6, comprising FIGS. 6A to 6F. Stem cell factor produced by cDC in the spleen is required for extramedullary stress erythropoiesis. We next investigated the molecular mechanism underlying cDC-dependent proerythroblast proliferation. Soluble mediators—i.e., Erythropoietin (Epo), stem cell factor (SCF) and bone morphogenetic protein 4 (BMP 4), IL-3 and GM-CSF—have each been implicated as necessary to expand erythroid progenitors during erythropoiesis. We first examined the profile of gene expression by cDC and non-DC subpopulations after magnetically sorting out the cell types from total splenic cells prepared at d1 (data now shown) or d2 (A) or after M1/69 infusion. The splenic cells were sorted into DCs (based on CD11c$^+$), T cells (CD90$^+$), B cells (B220$^+$) and remaining cell types, i.e., both CD45$^+$), hematopoietic origin cells and CD45$^-$ splenic stromal cells. We measured expression levels of mRNA encoding for SCF, Epo, BMP4, IL-3, and GM-CSF, respectively. Our data revealed that M1/69 treatment induced the expression of SCF exclusively by cDC (A). In contrast, cDC in the spleen did not upregulate mRNA for Epo, BMP4, IL-3 and GM-CSF (data now shown). (B-D) This suggests that SCF produced by splenic cDC via CD24 signaling contributes to M1/69-induced erythropoiesis. To investigate the role of SCF-c-Kit signaling in stress erythropoiesis, c-Kit KO mice were infused with αCD24 mAb. c-Kit deficiency resulted in an a markedly reduced percentage of reticulocytes in peripheral blood of mAb treated KO mice compared to treated wild type control mice when analyzed at d5 after mAb infusion (B). The importance of c-kit-mediated signaling in this process was further validated by the analysis of the gross appearance of spleens (C) and the accumulation of c-Kit$^-$ erythroid progenitors (CD45$^-$ Ter119$^+$, left panel in D) and c-Kit+ proerythroblasts (right panel in D) in the spleens at d5 after mAb infusion. As shown in C and D, the absence of c-Kit-SCF signaling axis resulted in the almost complete abrogation of M1/69-stimulated erythropoiesis. (E and F) We complemented the findings in c-Kit KO mice on the extramedullary stress erythropoiesis, by analyzing the impact of the pharmacological inhibitor of c-Kit signaling, imatinib (Gleevec). The drug (1 mg/kg) was administrated i.p. daily for 4 days into M1/69-treated WT mice. Consistent with the observations in c-Kit KO mice, administration of Imatinib into mAb treated WT B6 mice significantly reduced the reticulocytes in the blood (E) and inhibited the expansion/accumulation of CD45$^-$ Ter119$^+$ erythroid progenitors (left panel in F) and c-Kit$^+$ proerythroblasts (right panel in F) in the spleen. In summary, our data suggest that SCF produced by splenic cDC stimulated by engagement of the CD24 molecule on the cells with the M1/69 mAb promotes the expansion of c-Kit$^+$ erythroid progenitors in the spleen through a engagement of the c-Kit receptor on the early splenic erythroid progenitors.

Figure 7A:
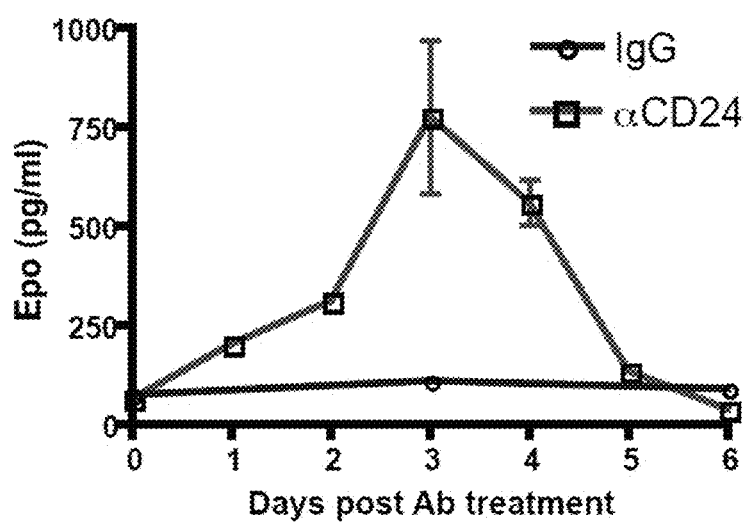
Figure 7B:
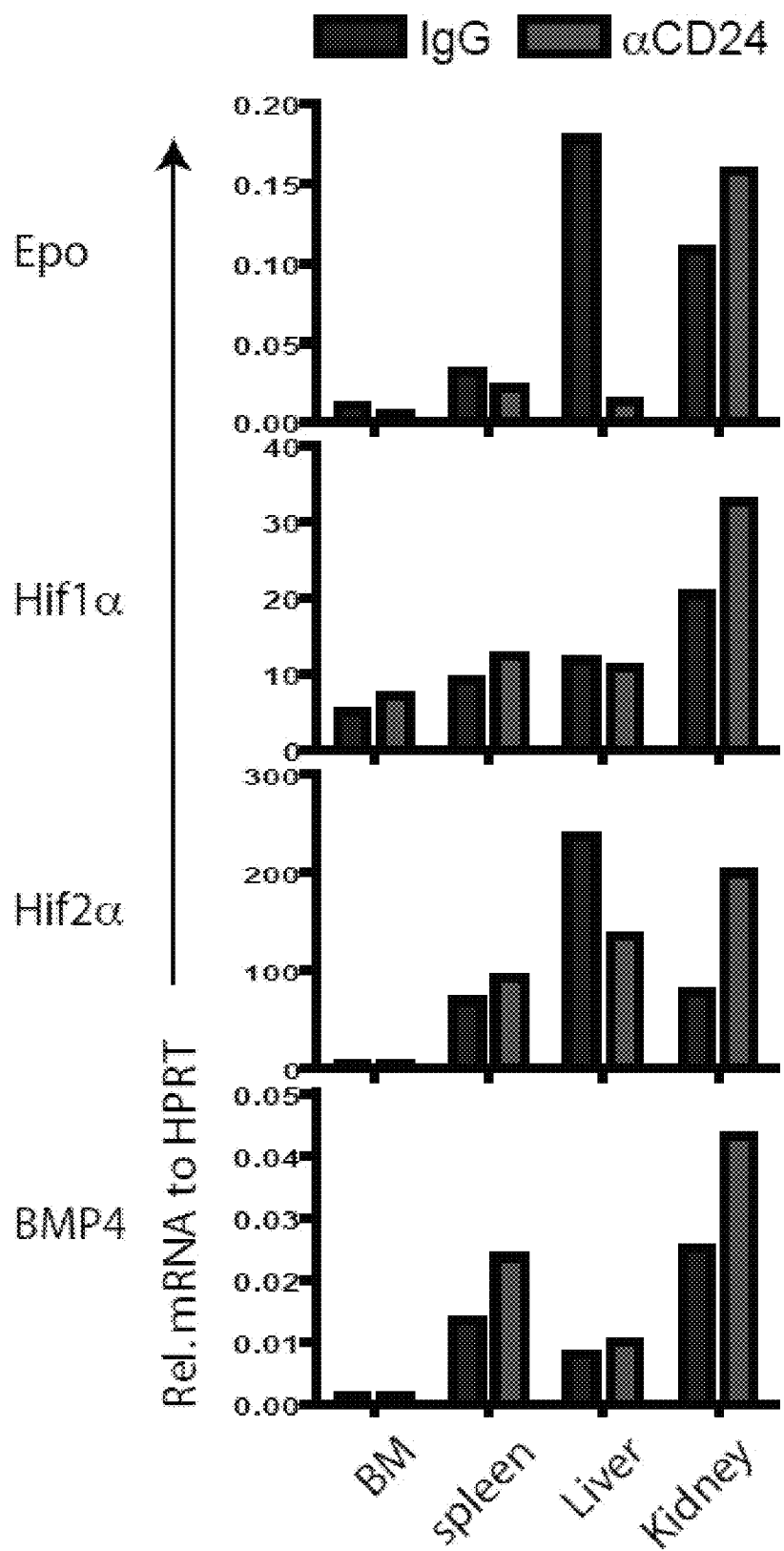
Figure 7C:
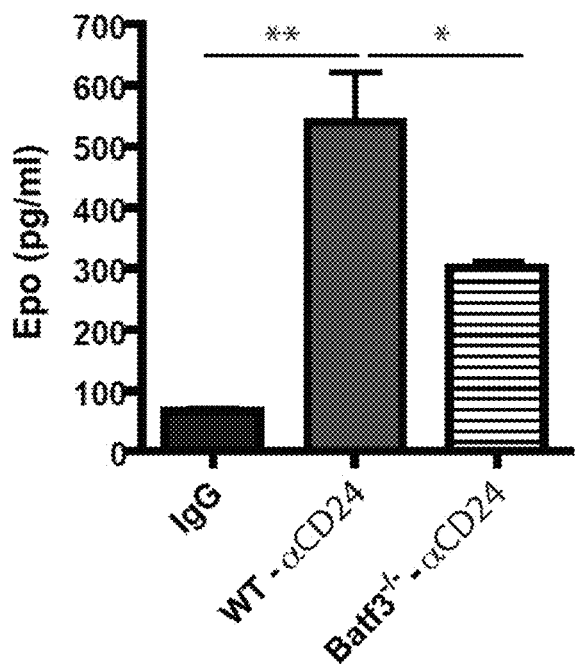
Figure 7D:
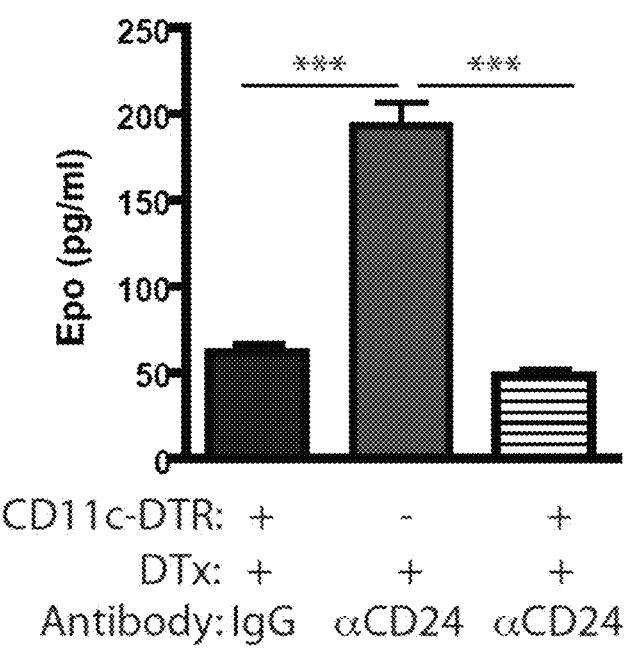
Figure 7E:
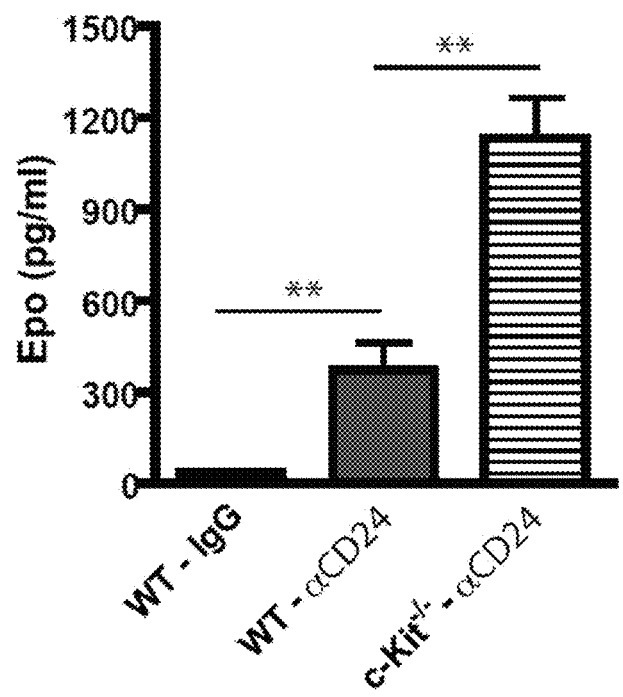

FIG. 7, comprising FIGS. 7A to 7E. Stress erythropoiesis triggered by M1/69 treatment requires Epo production by the kidneys, and Epo production is in turn dependent on the presence of cDC. Epo is a glycoprotein hormone that serves as a primary regulator of differentiation, proliferation, and survival of erythroid progenitor cells, and is made mainly by stromal cells within the kidneys. Epo and c-Kit signaling are both necessary for efficient erythropoiesis and work synergistically in this process. To fully account for the robust expansion of erythroid lineage progenitor cells in the spleen and the subsequent reticulocytosis following mAb treatment, we postulated that engagement of CD24 stimulates directly or indirectly Epo production by stromal cells in the kidney, which acts in concert with SCF produced locally in spleen to orchestrate extramedullary hematopoiesis. (A) When serum Epo levels were measured after M1/69 injection, we indeed detected a robust increase in Epo, peaking d3 after injection and then gradually decreasing over the several days. This burst of Epo production, as expected, proceeds the appearance of reticulocytes in the peripheral blood (see FIG. 2). (B) In FIG. 6, we have demonstrated that cDCs are critical in stress erythropoiesis induced by M1/69 treatment at least via the provision of SCF to stimulate the expansion of c-Kit receptor-expressing erythroid progenitors in the spleen. We reasoned that in parallel to splenic cDC, the counterpart of cDC subsets in the kidney may play a crucial role in promoting the production of Epo by epo-producing renal stromal cells. To test this hypothesis, we first measured Epo levels in the circulation of mice deficient in cDC, either genetically (i.e., Batf3 KO mice) or following cDC ablation (i.e., DTx-treated CD11c-DTR mice). We found a significant decrease in Epo production in Batf3 KO mice (C) and nearly complete ablation of Epo production in DTx-treated CD11c-DTR mice (D). These data demonstrate that cDCs localized in respective tissues play a crucial role in CD24-mediated stress erythropoiesis via at least stimulation of Epo induction in the kidneys and SCF production in the spleen. To dissect the contribution of Epo and SCF, respectively, we measured Epo concentration in c-Kit KO mice, which have an intact cDC compartment in the kidney (data not shown). In stark contrast to the absence of the expansion of c-Kit⁺ erythroid progenitors in the spleen, M1/69 treated c-Kit KO mice have demonstrated an elevated Epo level in the circulation (FIG. 7E). This is in keeping with the failure of expansion of c-Kit⁺ erythroid progenitors in the spleens of c-Kit KO mice which would be the primary consumers of Epo through binding of Epo to its receptor on the cells. This result indicates that the production of Epo alone, although necessary, is not sufficient to induce extramedullary stress erythropoiesis after CD24 engagement.

Figure 8:
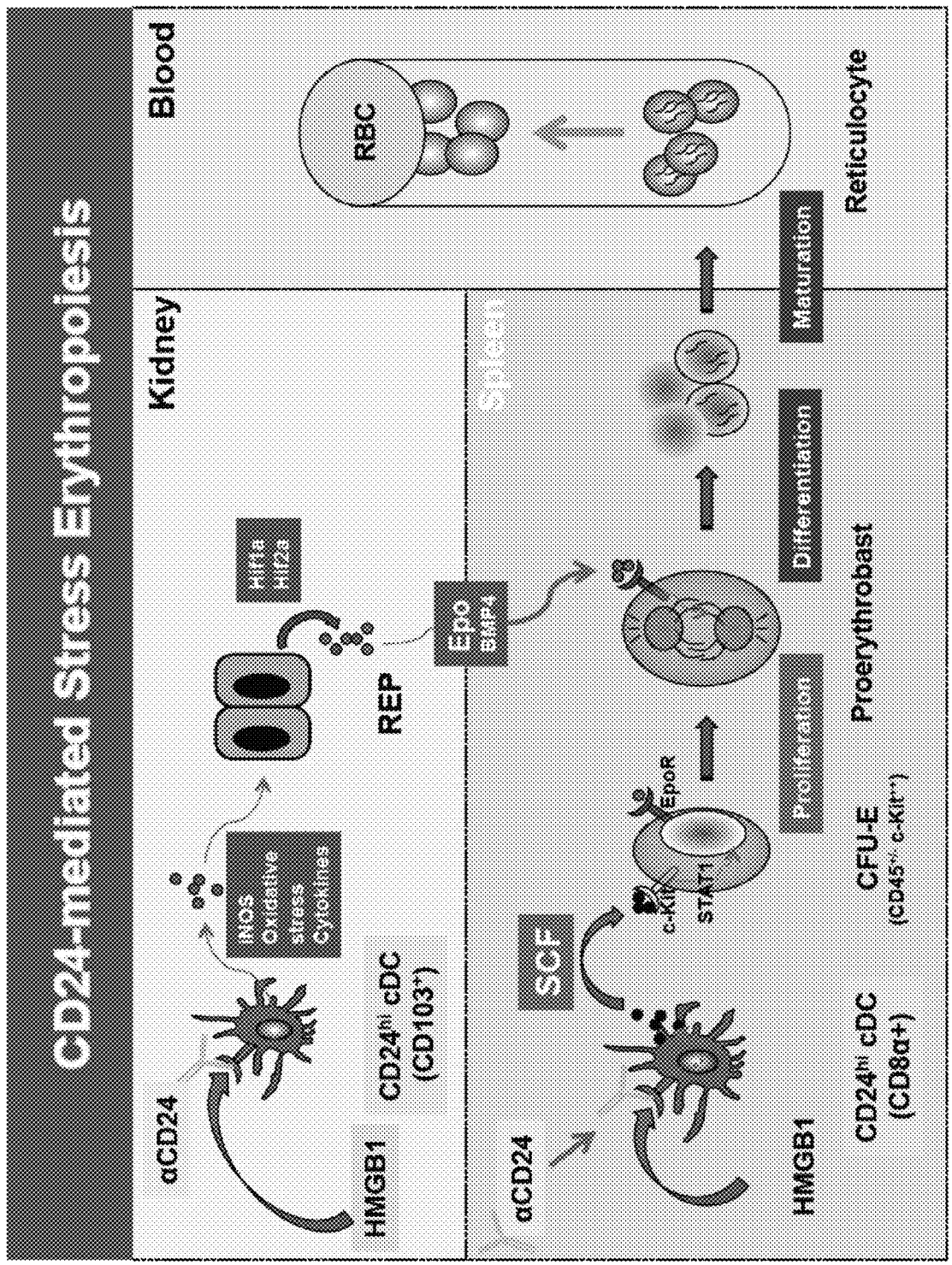

FIG. 8. Model for CD24-mediated stress erythropoiesis in vivo.

Without wishing to be bound by any particular theory, this schematic depicts a novel model for extramedullary stress erythropoiesis using an agonist of CD24 (the monoclonal antibody M1/69 in this schematic).

Figure 1A:
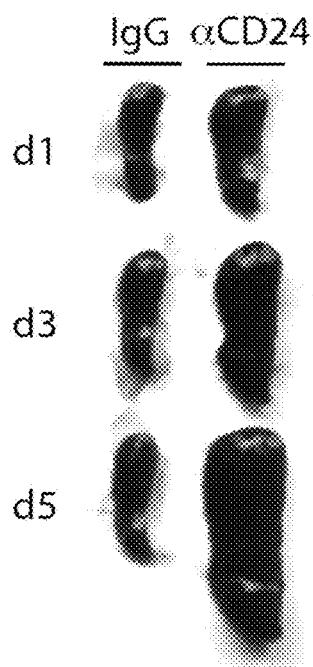
FIG. 1, comprising FIGS. 1A to 1E. Administration of the anti-CD24 mAb induces stress erythropoiesis in mice, and expression of CD 24 by cells of hematopoietic origin is required for induction of extra medullary hematopoiesis.
Figure 1B:
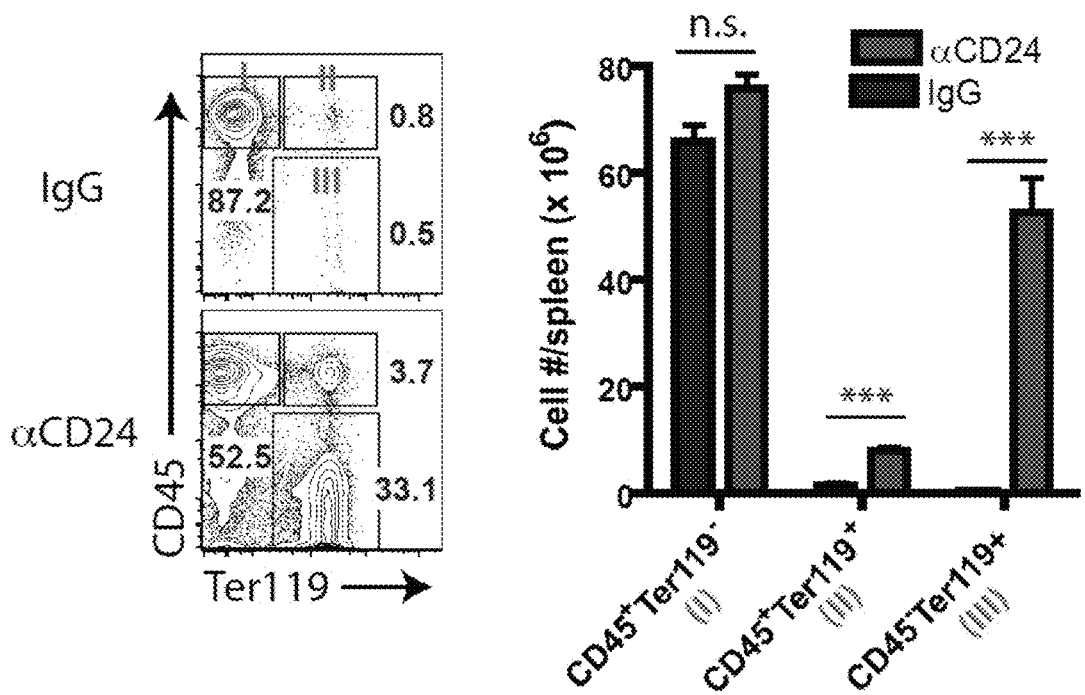
Figure 1C:
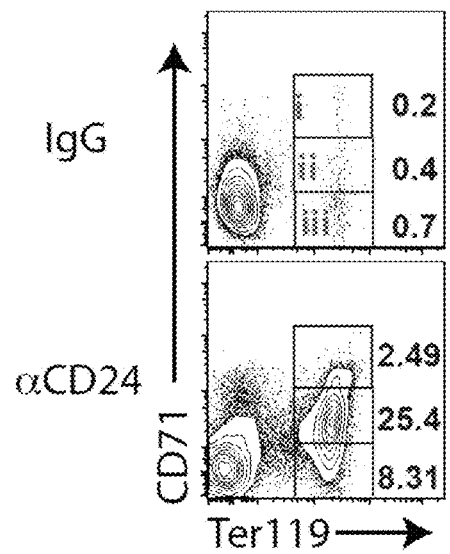
Figure 1D:
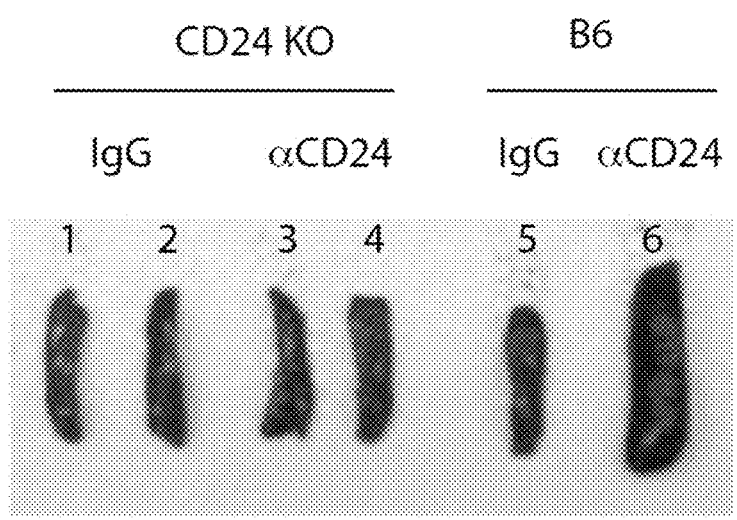
Figure 9A:
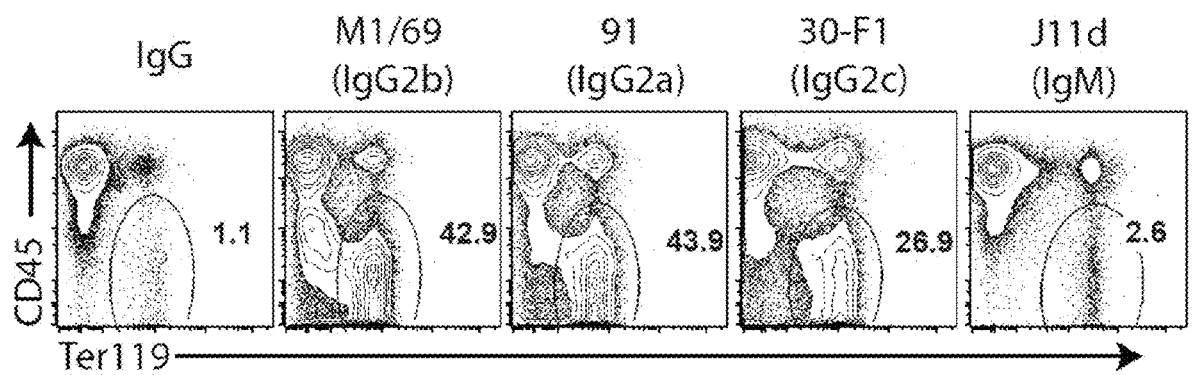
Figure 9B:
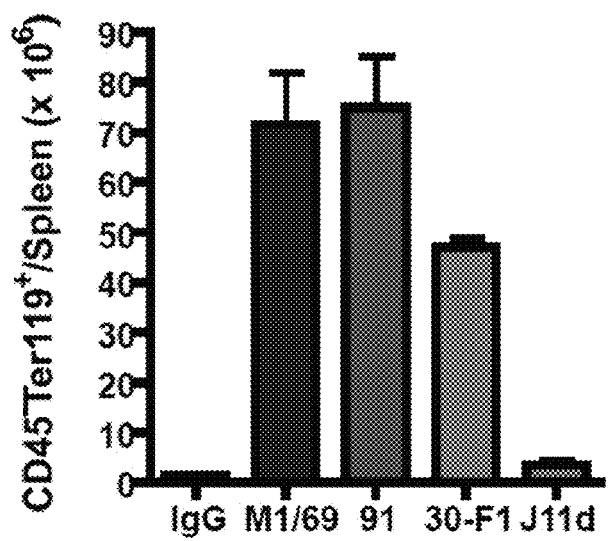

FIG. 9, comprising FIGS. 9A to 9B (also referred to as Supplemental FIG. 1A to 1B). Analysis of the stimulation of splenic erythrocyte progenitor (Ter119⁺CD45⁻ cells) expansion in the spleen following administration of M1/69 or 1 of 3 other monoclonal anti-CD24 antibodies, 91, 30-F 1, and J11 d, respectively. These data are included in Supplemental FIGS. 1A and 1B.

Figure 10:
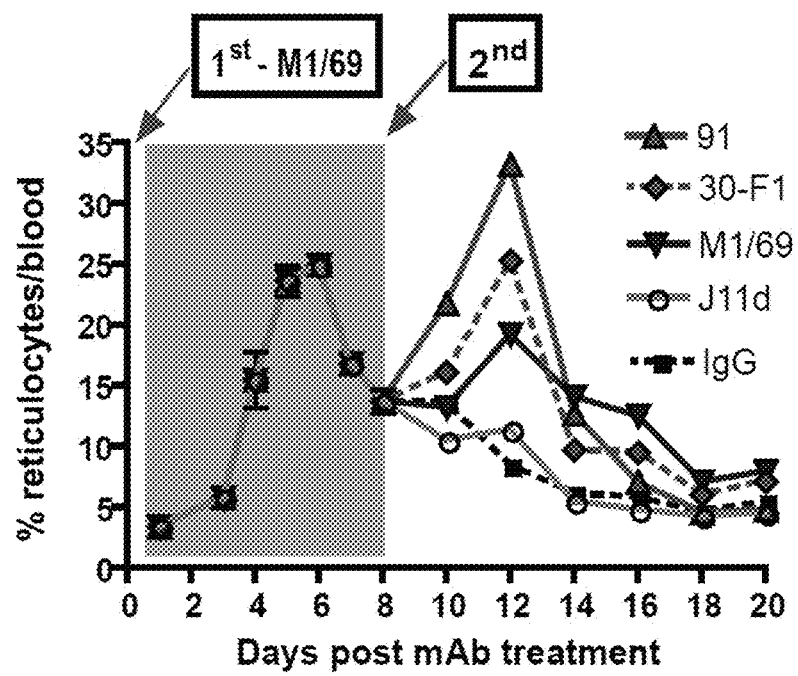

FIG. 10 (also referred to as Supplemental FIG. 2). Demonstrates the results of an analysis of the reticulocyte response to repeated administration of monoclonal antibody.

Figure 11:
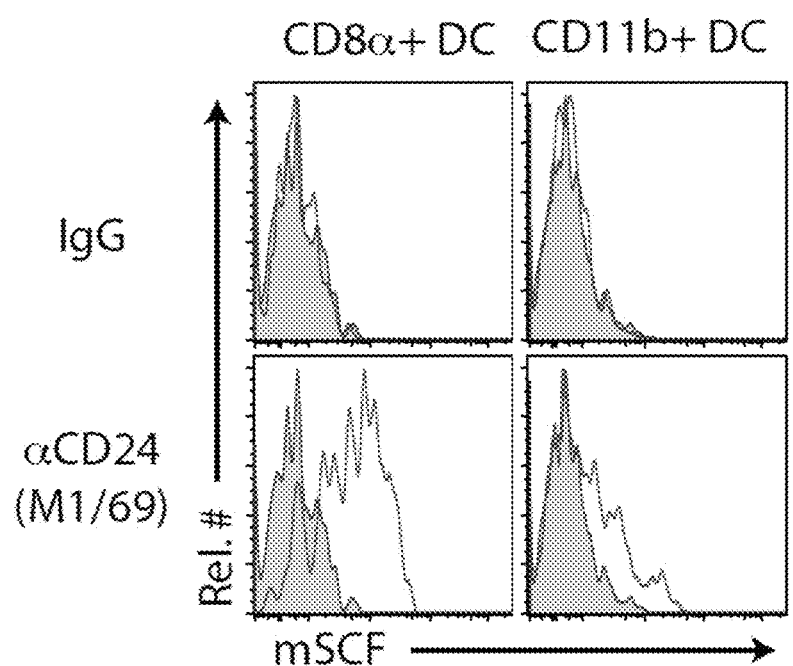

FIG. 11 (also referred to as Supplemental FIG. 3). Isolated conventional dendritic cells from the spleens of mice were treated with anti-CD24 monoclonal antibody overnight in cultures. We monitored the expression of the murine stem cell factor (mSCF) on the splenic CD8α⁺ DC subset and the more abundant CD8α⁻CD11b⁺ splenic DCs. As the figure indicates, mSCF is abundantly expressed on the surface of CD8α⁺ DC subset.

Figure 4A:
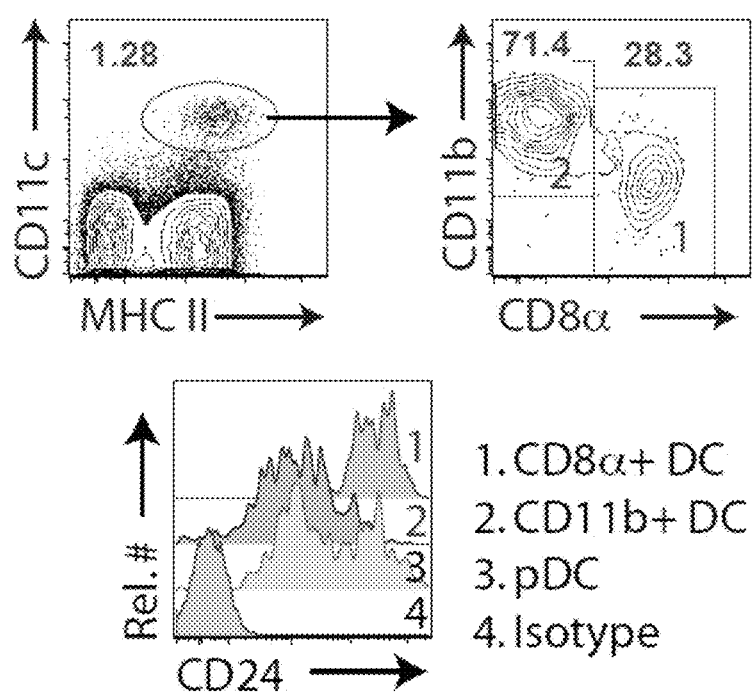
Figure 4B:
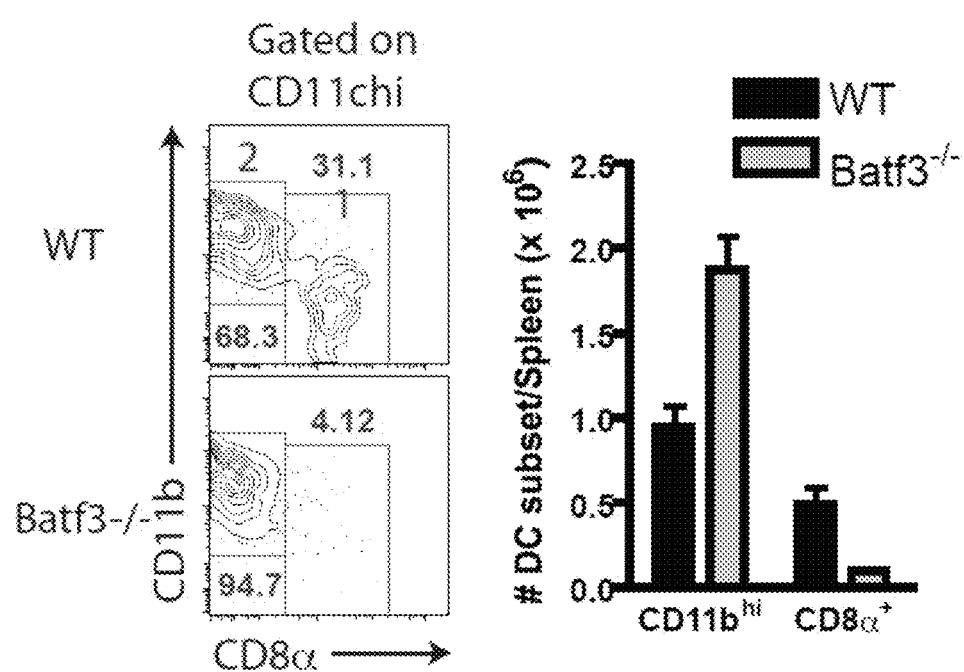
Figure 4C:
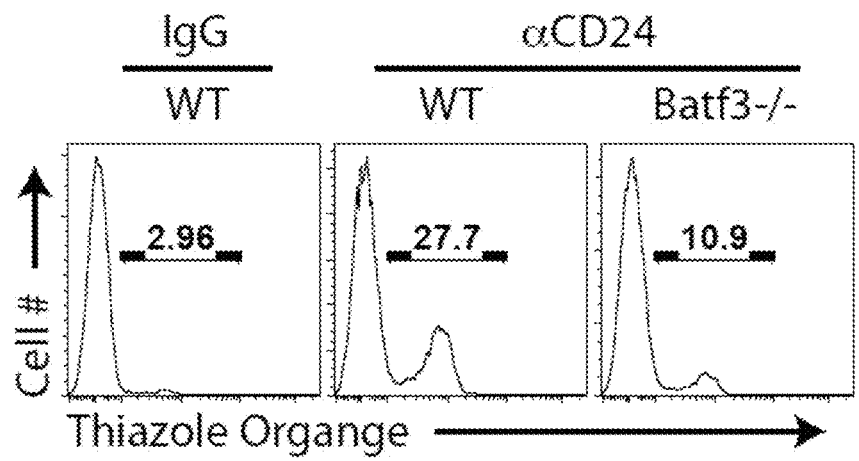
Figure 4D:
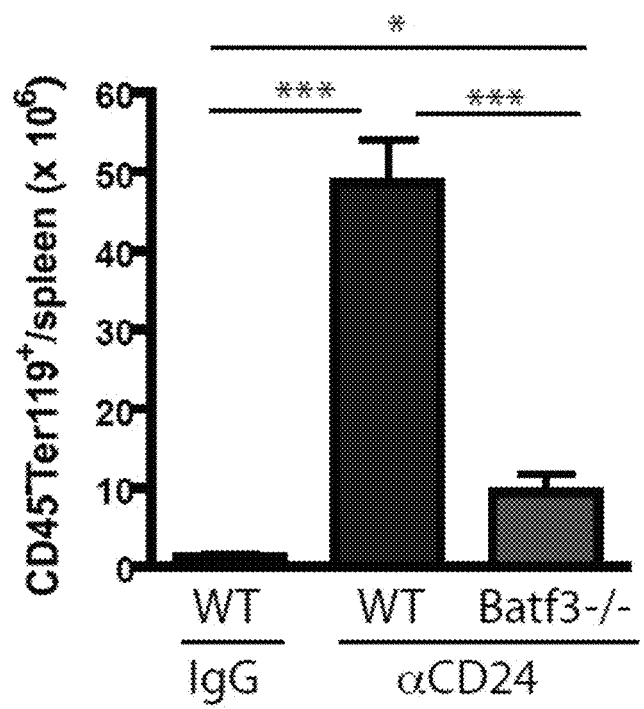
Figure 4E:
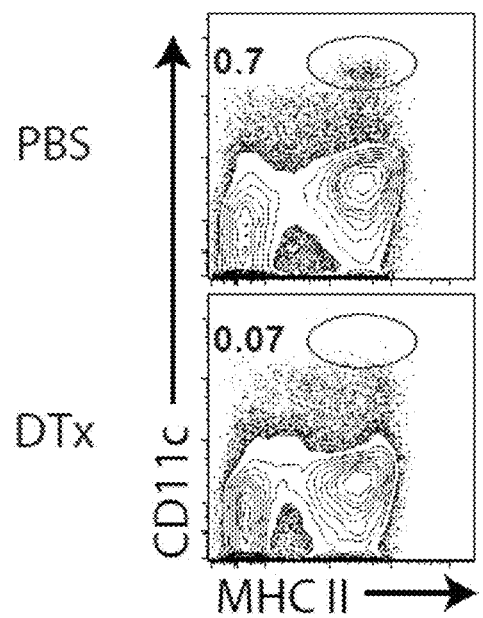
Figure 4F:
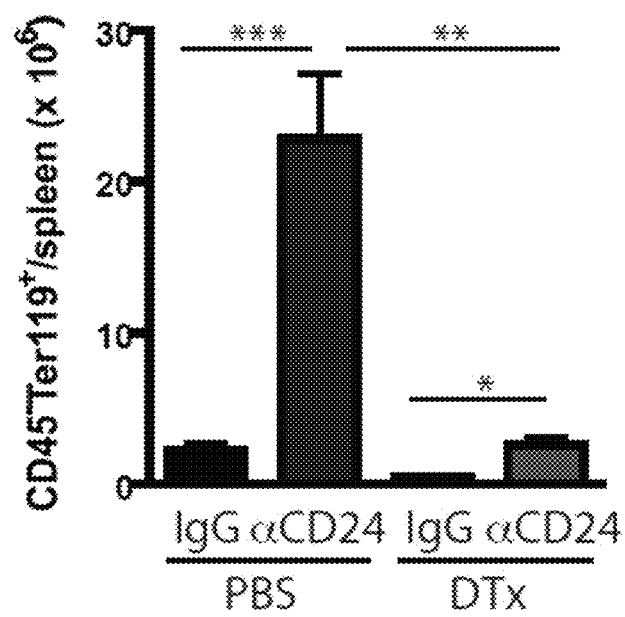
Figure 5A:
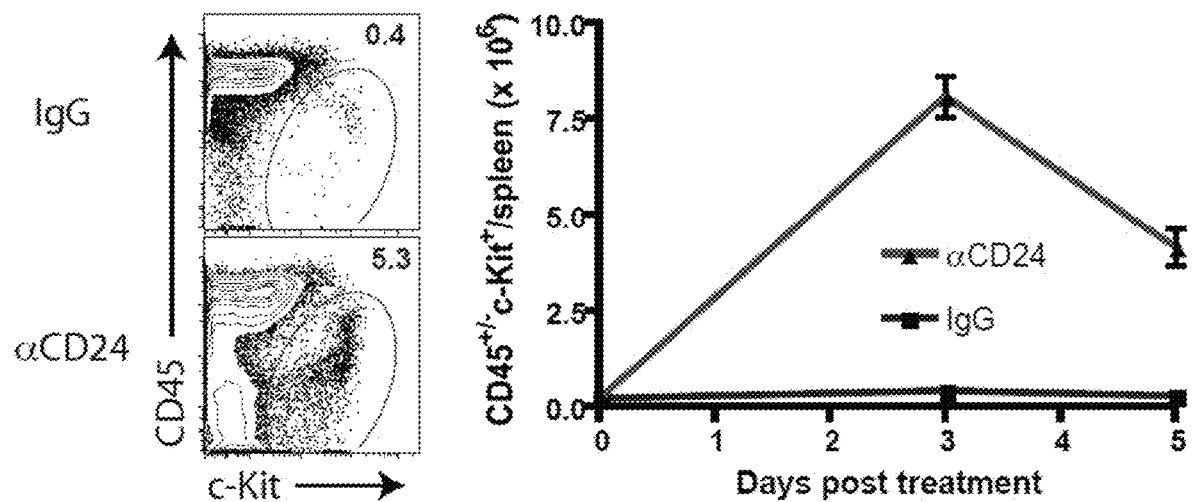
Figure 5B:
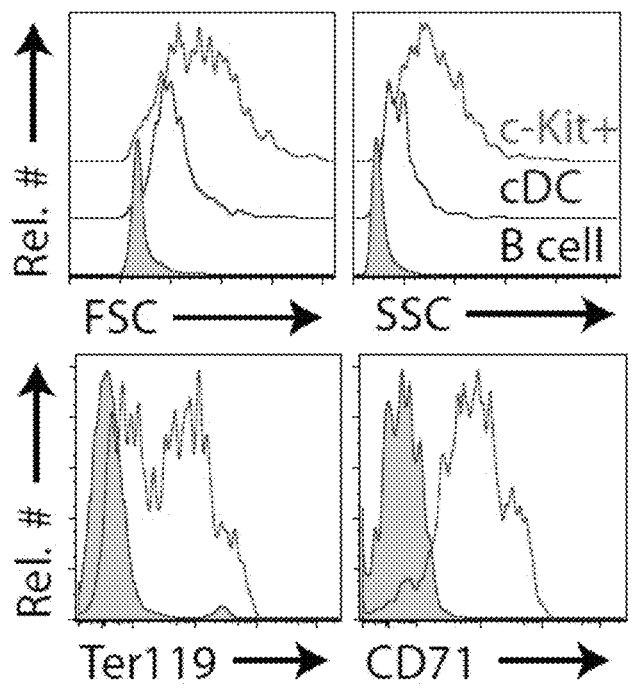
Figure 5C:
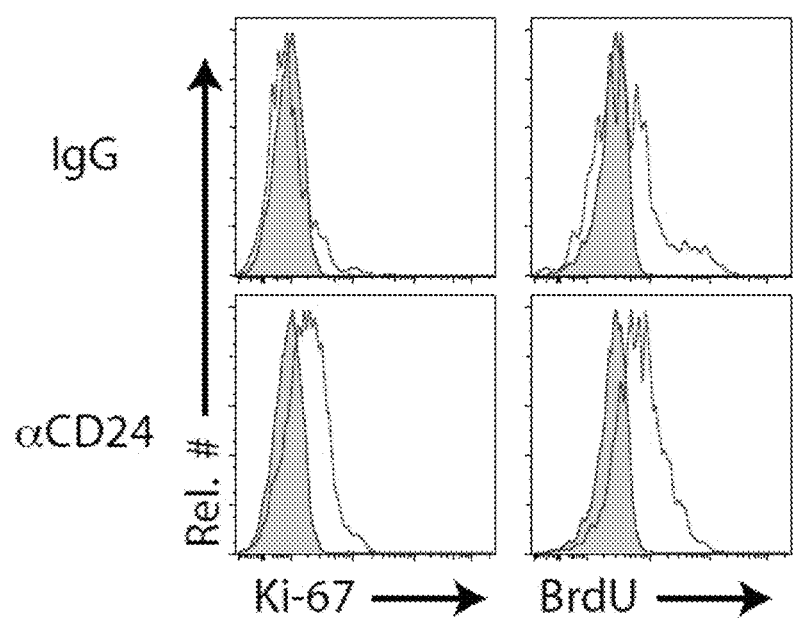
Figure 5D:
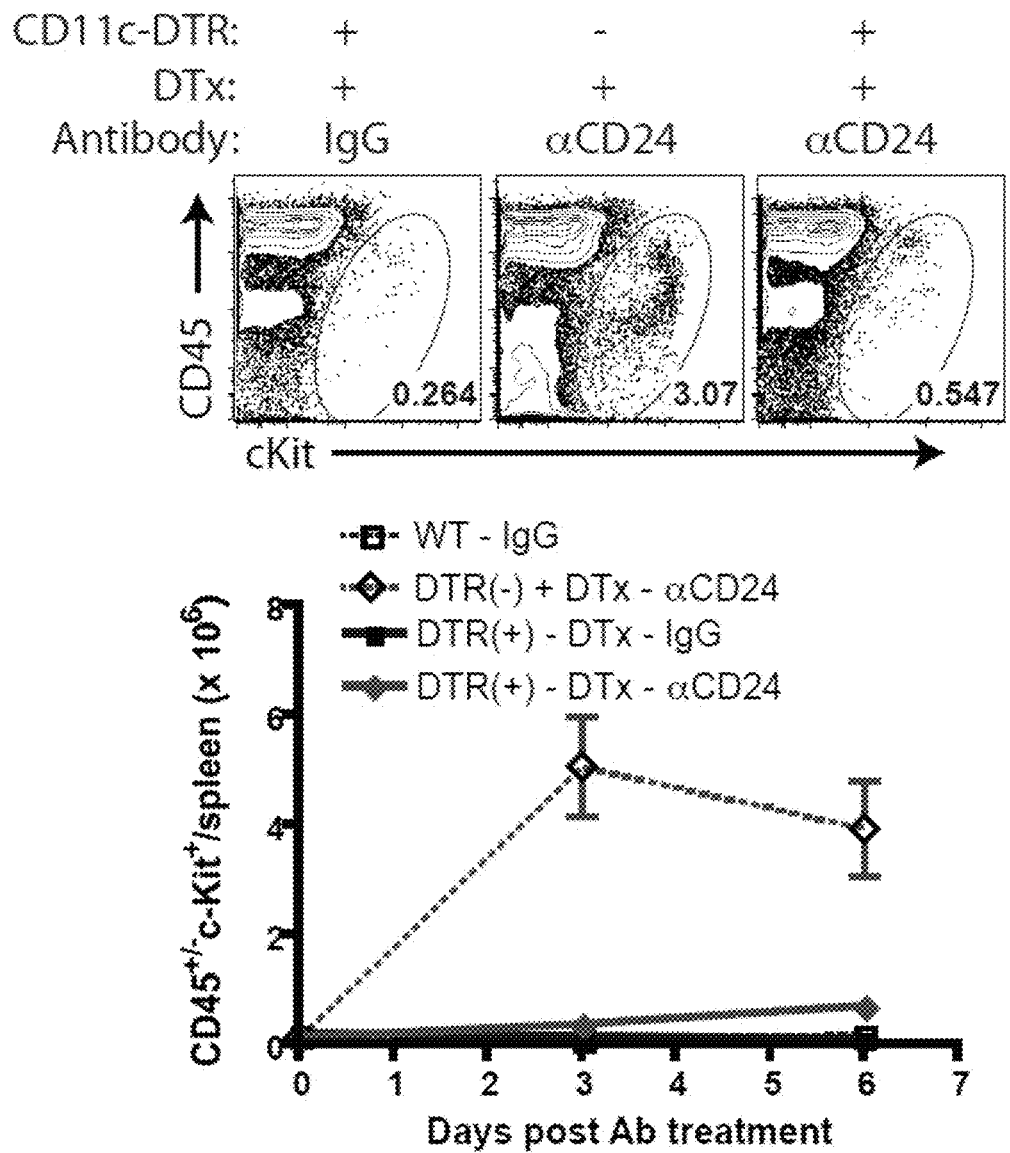
Figure 6A:
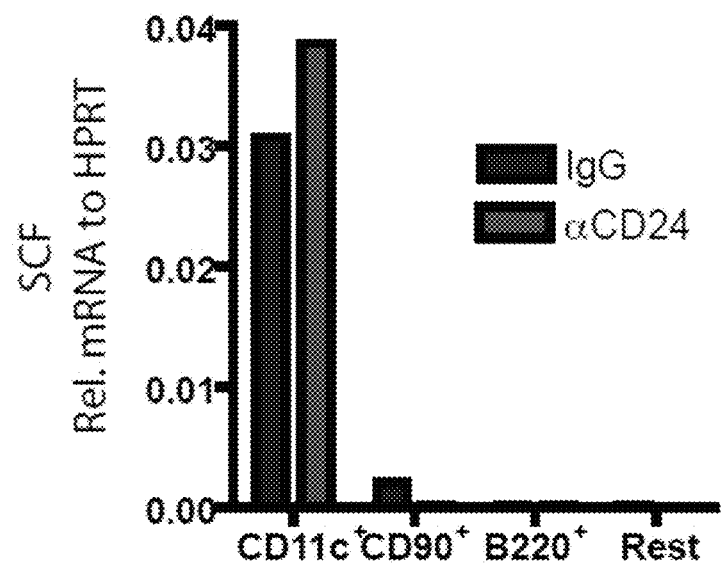
Figure 6B:
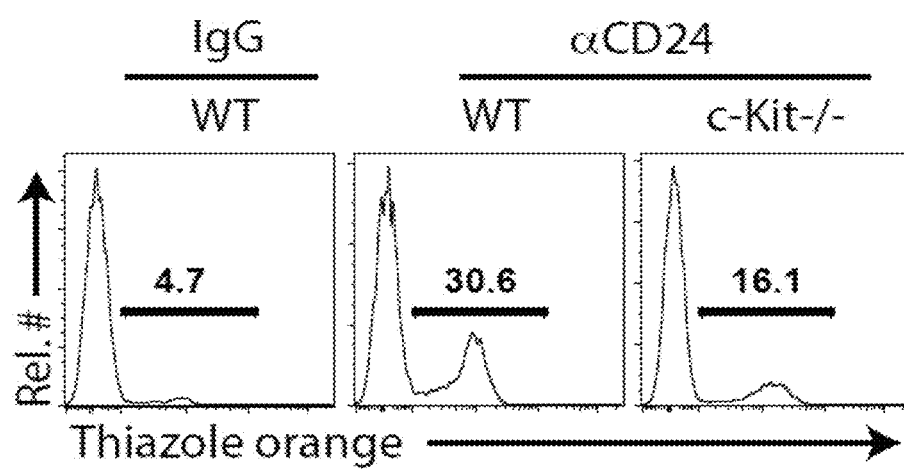
Figure 6C:
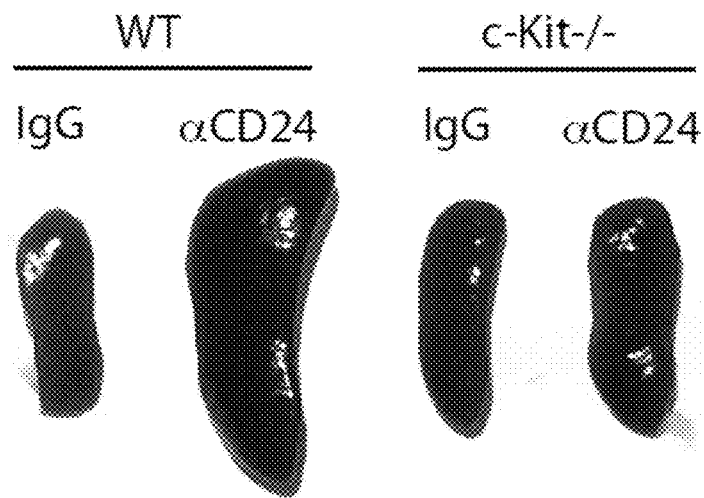
Figure 6D:
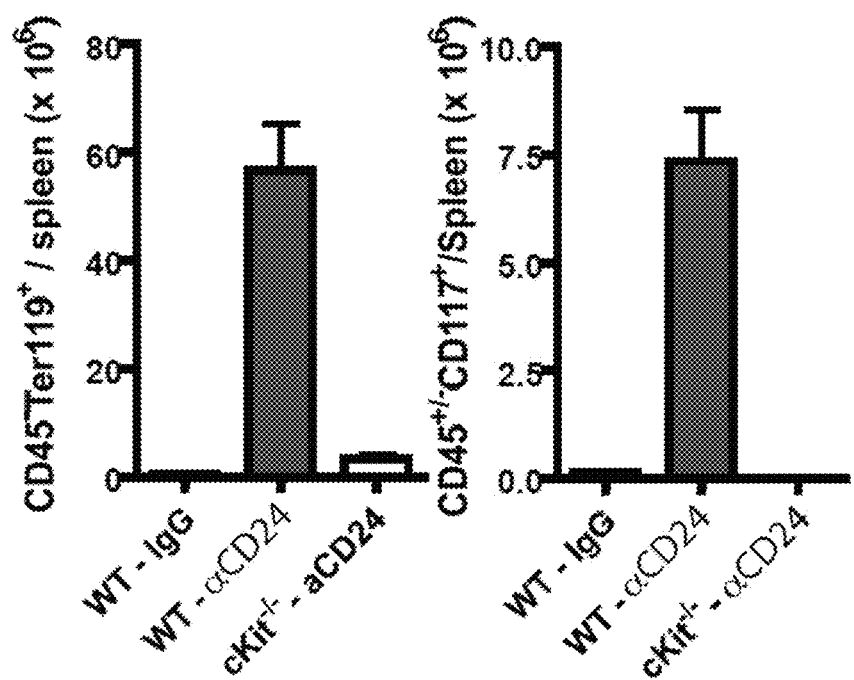
Figure 6E:
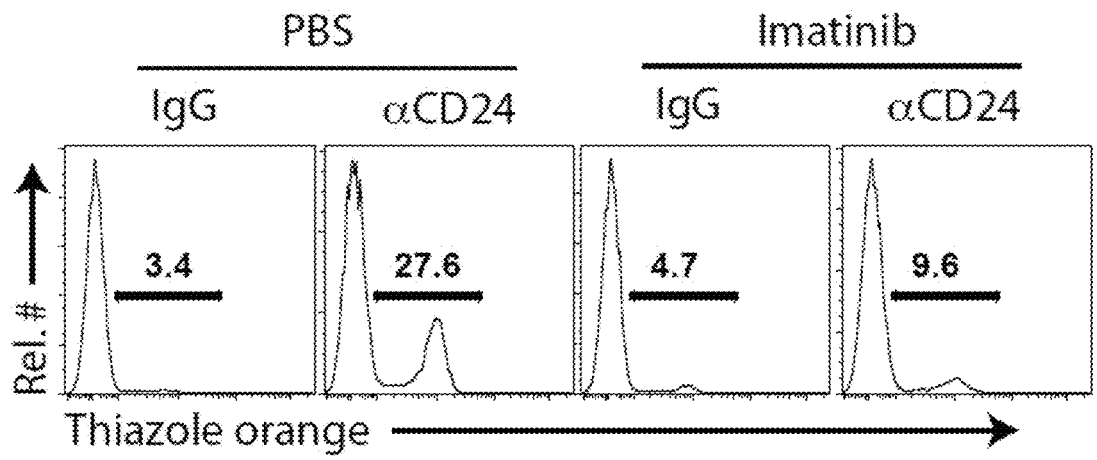
Figure 6F:
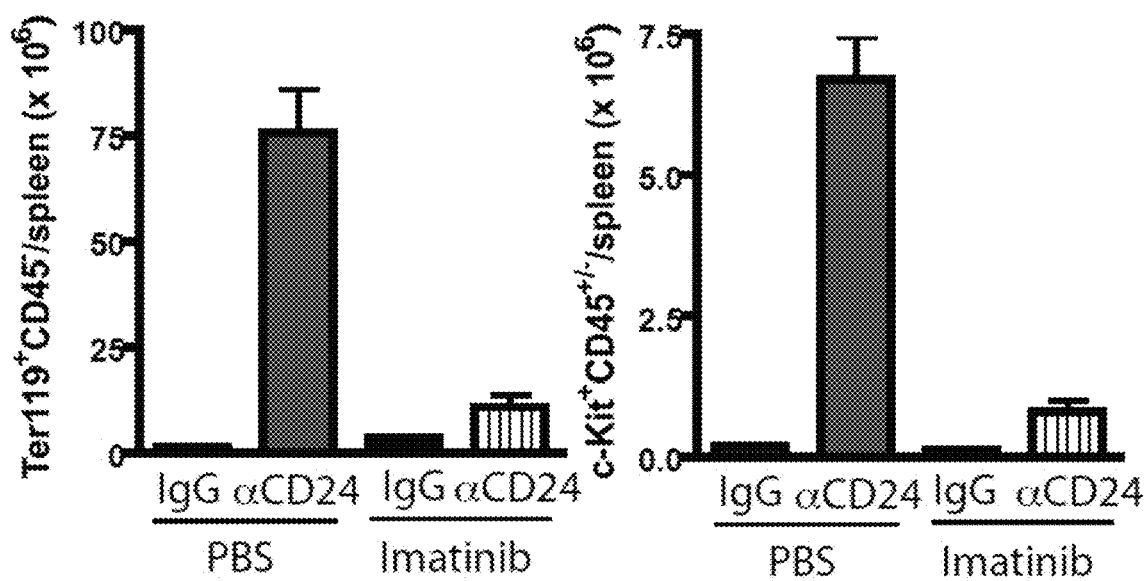
Figure 12A:
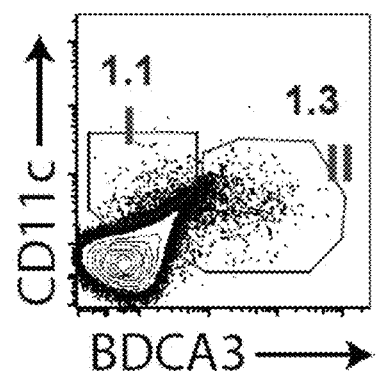
Figure 12B:
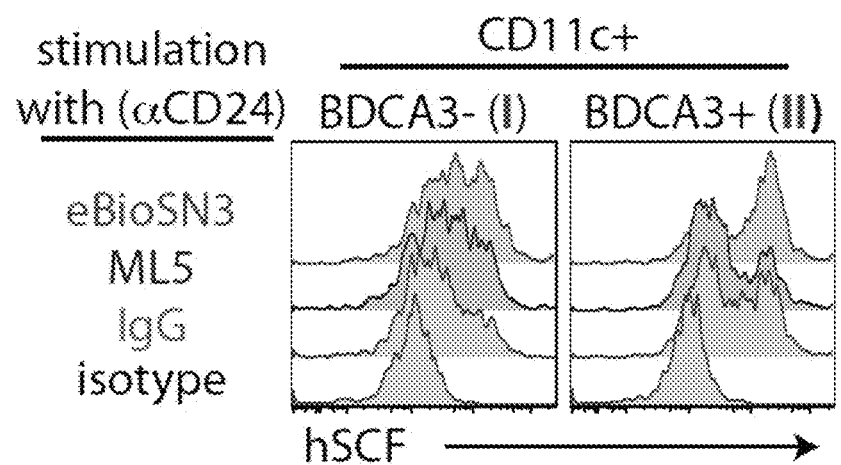

FIG. 12, comprising FIGS. 12A to 12B (also referred to as Supplemental FIG. 4A to 4B). A strategy was employed for generating BDCA3⁺ DC from human peripheral blood mononuclear cells in vitro using a cocktail of growth factors consisting of GM-CSF, IL-4, SCF, and Flt3L. These growth factors are highly potent stimulators of proliferation and differentiation of circulating mononuclear stem cells into a variety of cell types. Nonetheless, as Supplemental FIG. 4A demonstrates we can detect a small population of BDCA3⁺ DC-like cells in in vitro culture with a larger population of BDCA3⁻ cells. As Supplemental FIG. 4B demonstrates we can detect up-regulation of hSCF in response to treatment with 2 different monoclonal antibodies to human CD24: eBioSN3 and ML5. As Supplemental FIG. 4 B indicates the eBioSN3 monoclonal antibody regulates hSCF expression selectively on BDCA3⁺ DC. It will also note that the background expression of cell surface hSCF is high in both DC subsets. This we believe is due to the strong growth promoting activity of the growth factor cocktails. We anticipate that when this analysis is repeated with resting BDCA3⁺ DC isolated from human spleen, the background will be considerably lower. Nevertheless, these findings demonstrate that the corresponding up-regulation of cell surface hSCF by engagement of the CD24 receptor occurs as well in the corresponding population of human dendritic cells.

DETAILED DESCRIPTION

Abbreviations and Acronyms
Ab—antibody
BM—bone marrow
BMP—bone morphogenic protein
CD—cluster of differentiation
CRF—chronic renal failure
cDC—conventional DC
DC—dendritic cell
DTR—diphtheria toxin receptor
DTx—diphtheria toxin
EPO—erythropoietin
Flt3—Fms-Like Tyrosine Kinase 3
Flt3L—Flt3 Ligand
FSC—forward scatter
GM-CSF—granulocyte macrophage colony stimulating factor, also referred to as G-CSF
HMGB1—high mobility group protein group B1, also referred to as high mobility group protein
hEPO—human erythropoietin
hSCF—human stem cell factor
HSP—heat shock protein
KO—knockout
HSA—heat stable antigen (also referred to as CD24)
IL-3—interleukin-3
IL-4—interleukin-4
mAb—monoclonal antibody
mSCF—murine stem cell factor
RBC—red blood cell, also referred to as erythrocyte
SCF—stem cell factor
SSC—side scatter
WT—wild type
Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

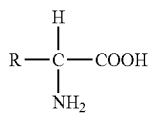

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, CSF, blood, serum, plasma, gastric aspirates, throat swabs, skin, hair, tissue, blood, plasma, serum, cells, sweat and urine.

"Blood components" refers to main/important components such as red cells, white cells, platelets, and plasma and to other components that can be derived such as serum.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above, as well as to biologics. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;

IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The term "directed against CD24" means that the compound being recited, whether a small molecule, drug, prodrug, or an antibody, or a biologically active fragment or homolog thereof, binds to and/or activates CD24 or stimulates its activity, or all of the above.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

The term "erythropoietin" as used herein includes EPO of every origin, especially human or animal EPO. The term used herein encompasses not only the naturally occurring, that is wild-type forms of EPO, but also its homologues, fragments, derivatives, analogs, modifications, muteins, mutants or others, as long as they show the biological effects of wild-type erythropoietin or an activity described herein. It also includes synthetic EPO.

As used herein, an "essentially pure" preparation of a particular protein or peptide is a preparation wherein at least about 95%, and preferably at least about 99%, by weight, of the protein or peptide in the preparation is the particular protein or peptide.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound of the invention to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "per application" as used herein refers to administration of a compositions, drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "promoter/regulatory sequence" means a nucleic acid sequence which is required for expression of a gene product operably linked to the promoter/ regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "stimulate CD24" refers to synthesis, levels, activity, or function of the CD24; and for synthesis or levels can refer to mRNA and protein. Additionally, the terms "stimulate" or "stimulation" mean to cause an increase in synthesis, levels, activity, or function of the molecule or cell of interest, based on the context in which the term is used.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1× SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1× SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide that has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

As used herein, the term "treating" can include prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced. By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention is directed to compositions and methods for regulating erythropoiesis by stimulating CD24 or a CD24 pathway. One of ordinary skill in the art will appreciate that the methods described herein can be modified in some instances and practiced with the invention.

In some embodiments, the therapeutic methods described herein may be used to promote stress erythropoiesis. In some embodiments, the therapeutic methods described herein may be used to treat conditions responding to hypoxic stress by administering to a subject in need thereof a therapeutic composition. Conditions responding to hypoxic stress include, but are not limited to, anemia, blood loss, and aging. According to the present invention, potential therapeutic agents may be screened for the ability to stimulate splenic erythrocyte progenitor expansion in the spleen.

In addition, potential therapeutic agents may be screened for the ability to increase the expression level of the human stem cell factor (hSCF) on the human splenic DC expressing the cell surface molecule BDCA3 (CD141).

An agonist of CD24 includes any compound or group of compounds that can stimulate stress erythropoiesis as disclosed herein using antibodies directed against CD24. Agonists of CD24 activity can include, for example, peptides, antisense oligonucleotides, nucleic acids encoding peptides described herein, aptamers, antibodies, kinase inhibitors, and drugs/agents/compounds. Many assays and methods are described herein or are known in the art that allow one of ordinary skill in the art to monitor whether a compound regulates the components of the signal transduction and regulatory pathway.

In some embodiments, the present invention is a method of enhancing the activity of erythrocytic stem cell precursors by administering to a subject in need thereof a fragment of the monoclonal antibody (mAb) against CD24. According to some aspects of the present invention, compounds of interest include, but are not limited to, the F(ab)2 fragment of the monoclonal antibody (mAb) to CD24.

In some instances, the production of cells including, but not limited to, erythrocytes and erythroid progenitor cells is promoted. The production of any convenient erythroid progenitor cells may be promoted by the method. In some instances, the erythroid progenitor cells of interest include, but are not limited to, basophilic erythroblasts of the spleen, in some instances polychromatophilic erythroblasts, and in some instances, the erythroid progenitor cells are orthochromatic erythroblasts.

According to some aspects of the invention, the CD24 being engaged by the therapeutic compound is on a subset of splenic DCs.

In some embodiments, the present invention is a method of enhancing the activity of erythrocytic stem cell precursors and promoting the production of erythrocytes and erythroid progenitor cells by administering to a subject in need thereof an effective amount of compound or peptide that is a downstream component of the CD24 signal pathway.

The present invention further encompasses use of the yeast two-hybrid system to identify regulators of the proteins and pathways described herein. Such regulators can be drugs, compounds, peptides, nucleic acids, etc. Such regulators can include endogenous regulators. Generally, the yeast two-hybrid assay can identify novel protein-protein interactions and compounds that alter those interactions. By using a number of different proteins as potential binding partners, it is possible to detect interactions that were previously uncharacterized. Additionally, the yeast two-hybrid assay can be used to characterize interactions already known to occur. Characterization could include determining which protein domains are responsible for the interaction, by using truncated proteins, or under what conditions interactions take place, by altering the intracellular environment. These assays can also be used to screen modulators of the interactions.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the peptide may be added to a cell along with the compound to be screened for a particular activity and the ability of the compound to inhibit the activity of interest in the presence of the peptide indicates that the compound is an antagonist to the peptide. The peptide can be labeled, such as by radioactivity.

Anti-CD24 (ML5) (Santa Cruz Biotechnology) is a mouse monoclonal antibody raised against CD24 of human origin. This antibody can also be labeled or purchased with a label, such as conjugated with Alexa Fluor® 488. Unlabeled anti-CD24 mAbs can be obtained from the B cell panel of the V International Workshop on Human Leucocyte Differentiation Antigens.

Any convenient monoclonal antibody (mAb) against CD24 may be utilized. Alternatively, any convenient polyclonal antibody against CD24 may be utilized. Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120). Anti-CD24 antibodies, both polyclonal and monoclonal, suitable for use in the methods and compositions of the present invention are commercially available, for example, from Santa Cruz Biotechnology (Santa Cruz, Calif.), AbDSerotec (Kidlington, UK) and Life Span BioSciences, Inc (Seattle Wash.).

It will be appreciated that for human therapy or diagnostics, humanized antibodies are preferably used. Humanized forms of nonhuman (e.g., murine) antibodies are genetically engineered chimeric antibodies or antibody fragments having—preferably minimal—portions derived from nonhuman antibodies. Humanized antibodies include antibodies in which complementary determining regions of a human antibody (recipient antibody) are replaced by residues from a complementarity determining region of a nonhuman species (donor antibody) such as mouse, rat or rabbit having the desired functionality. In some instances, Fv framework residues of the human antibody are replaced by corresponding nonhuman residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a nonhuman antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing nonhuman antibodies are well known in the art. Generally, a humanized antibody has one or more amino acid residues introduced into it from a source which is nonhuman. These nonhuman amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a nonhuman species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage or yeast display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368:812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies are obtained, they may be tested for activity, for example via ELISA.

According to some aspects of the present invention, the method includes providing to the subject a therapeutic compound in combination with a pharmaceutically acceptable carrier.

According to some aspects of the present invention, the antibody or combination can be provided using any one of a variety of delivery methods. Delivery methods and suitable formulations are described herein below with respect to pharmaceutical compositions.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH$_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Antibodies and Their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

The antigenic fragments of the proteins of the invention may include, for example, peptide antigens that are at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 or up to about 200 amino acids in length. Of course, these are prepared based on the length of the starting protein or peptide. Also included are full-length unprocessed protein as well as mature processed protein. These various length antigenic fragments may be designed in tandem order of linear amino acid sequence of the immunogen of choice, such as SAS1R, or staggered in linear sequence of the protein. In addition, antibodies to three-dimensional epitopes, i.e., non-linear epitopes, can also be prepared, based on, e.g., crystallographic data of proteins. Hosts may also be injected with peptides of different lengths encompassing a desired target sequence.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in Monoclonal Antibodies and Cancer Therapy, Alan R. Liss, Inc., pp. 77-96) may be employed to produce human monoclonal antibodies. In another embodiment, monoclonal antibodies are produced in germ-free animals.

In one embodiment, any new monoclonal antibody described herein, or made using the methods described herein, and the hybridomas making the antibodies, as well as those not described herein, will be deposited with the American Type Culture Collection (10801 University Boulevard, Manassas, Va. 20110-2209) and assigned Accession Numbers. The deposits will be maintained under the terms of the Budapest Treaty on the International Recognition of the Deposit of Microorganisms for the Purposes of Patent Procedure and made available for use under those terms. This assures maintenance of a viable culture of the deposit for 30 years from the date of deposit. The deposits will be made available by ATCC under the terms of the Budapest Treaty, and subject to an agreement between the University of Virginia and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC section 122 and the Commissioner's rules pursuant thereto (including 37 CFR section 1.14 with particular reference to 886 OG 638). The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. Nucleic acid and amino acid sequences will be deposited with GenBank and made accessible to the public.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in Monoclonal Antibodies and Cancer Therapy, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

In another embodiment, this invention provides for fully human antibodies. Human antibodies consist entirely of characteristically human polypeptide sequences.

The human antibodies of this invention can be produced in using a wide variety of methods (see, e.g., U.S. Pat. No. 5,001,065, for review).

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, *Blood*, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, *Critical Rev. in Immunol.* 12(3,4):125-168) and the references cited therein. Further, the antibody of the invention may be "humanized" using the technology described in Wright et al., (supra) and in the references cited therein, and in Gu et al. (1997, *Thrombosis and Hematocyst* 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, *Adv. Immunol.* 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol.248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the a-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$—,$C_8$— or $C_{18}$— silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification,* Harcourt Brace Jovanovich, San Diego).

The invention further encompasses the use of aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)]. Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, high-throughput assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable sub-domains (15-50 amino acids long). This technology can be integrated with high throughput screening techniques such as phage display and reverse yeast two-hybrid traps.

The present application discloses compositions and methods for regulating the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2—S—CH2), diinethylene-sulfoxide (—CH2—SO—CH2), dimethylene-sulfone (—CH2—SO2-CH2), 2'—O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified. The term nucleic acid also specifically includes nucleic acids composed of bases other than the five biologically occurring bases (adenine, guanine, thymine, cytosine and uracil).

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

When used in vivo for therapy, the antibodies of the invention are administered to the subject in therapeutically effective amounts (i.e., amounts that have a desired therapeutic effect). In one aspect, they will be administered parenterally. The dose and dosage regimen will depend, for example, upon the degree of the anemia, the characteristics of the particular antibody or other compound used, e.g., its therapeutic index, the subject, and the subject's history. In one embodiment, at least one antibody or other agonist compound is administered once, or more than once, or even continuously over a period of 1-2 weeks. Optionally, the administration is made during the course of adjunct therapy such as antimicrobial treatment, or administration of, for example, a cytokine(s), or other EPO or erythropoiesis regulatory agent.

For parenteral administration, an antibody can be formulated, for example, in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

In one aspect, the invention provides for the use of IgM antibodies; however, IgG molecules by being smaller can be more able than IgM molecules to localize to certain types of infected cells. Therefore, in one aspect, IgG antibodies are useful in the practice of the invention.

The antibody compositions used can be formulated and dosages established in a fashion consistent with good medical practice taking into account the condition or disorder to be treated, the condition of the individual patient, the site of delivery of the composition, the method of administration, and other factors known to practitioners. The antibody compositions are prepared for administration according to the description of preparation of polypeptides for administration, infra.

As is well understood in the art, biospecific capture reagents include antibodies, binding fragments of antibodies which bind to activated integrin receptors on metastatic cells (e.g., single chain antibodies, Fab' fragments, F(ab)'2 fragments, and scFv proteins and affibodies (Affibody, Teknikringen 30, floor 6, Box 700 04, Stockholm SE-10044, Sweden; See U.S. Pat. No. 5,831,012, incorporated herein by reference in its entirety and for all purposes)). Depending on intended use, they also can include receptors and other proteins that specifically bind another biomolecule.

The hybrid antibodies and hybrid antibody fragments include complete antibody molecules having full length heavy and light chains, or any fragment thereof, such as Fab, Fab', F(ab')2, Fd, scFv, antibody light chains and antibody heavy chains. Chimeric antibodies which have variable regions as described herein and constant regions from various species are also suitable. See for example, U.S. Application No. 20030022244. Initially, a predetermined target object is chosen to which an antibody can be raised. Techniques for generating monoclonal antibodies directed to target objects are well known to those skilled in the art. Examples of such techniques include, but are not limited to, those involving display libraries, xeno or humab mice, hybridomas, and the like. Target objects include any substance which is capable of exhibiting antigenicity and are usually proteins or protein polysaccharides. Examples include receptors, enzymes, hormones, growth factors, peptides and the like. It should be understood that not only are naturally occurring antibodies suitable for use in accordance with the present disclosure, but engineered antibodies and antibody fragments which are directed to a predetermined object are also suitable.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

In accordance with one embodiment, a method of treating a subject in need of treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the subject. While the precise dosage administered will vary depending upon any number of factors, including, but not limited to, the type of animal and type of disease state being treated, the age of the subject and the route of administration. In one aspect, the dosage of the compound will vary from about 1 mg to about 10 g per kilogram of body weight of the subject. In another aspect, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the subject, etc.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention, including those described in international patent application WO 2006/091535 (PCT/US2006/005970), the entirety of which is incorporated by reference herein.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as (β-alanine, β-Ala, bA, and βA, having the structure:

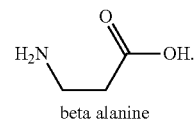

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N— and/or C— blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$—, $C_8$— or $C_{18}$— silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3'-, or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids can include various hydropathic indices. In one aspect, the hydropathic indices are within +/−2, in another they are within +/−1, and in one aspect, they are within +/−0.5.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) In one aspect, the replacement of amino acids with others of similar hydrophilicity is provided by the invention.

Other considerations include the size of the amino acid side chain. For example, it would generally not be preferable to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Linkers

Additionally, modifications encompassed by the invention include introduction of linkers or spacers between the targeting sequence of the binding moiety or binding polypeptide and a detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the antibody/peptide ligand complexes described herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The invention further provides cells transfected with the nucleic acid containing an enhancer/promoter combination of the invention.

Promoters may be coupled with other regulatory sequences/elements which, when bound to appropriate intracellular regulatory factors, enhance ("enhancers") or repress ("repressors") promoter-dependent transcription. A promoter, enhancer, or repressor, is said to be "operably linked" to a transgene when such element(s) control(s) or affect(s) transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, and other expression control elements, or any combination of such elements.

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis as the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000-fold from linked homologous or heterologous promoters. Enhancer elements often remain active even if their orientation is reversed (Li et al., J. Bio. Chem. 1990, 266: 6562-6570). Furthermore, unlike promoter elements, enhancers can be active when placed downstream from the transcription initiation site, e.g., within an intron, or even at a considerable distance from the promoter (Yutzey et al., Mol. and Cell. Bio. 1989, 9:1397-1405).

It is known in the art that some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence.

The present invention further relies on the fact that many enhancers of cellular genes work exclusively in a particular tissue or cell type. In addition, some enhancers become active only under specific conditions that are generated by the presence of an inducer such as a hormone or metal ion. Because of these differences in the specificities of cellular enhancers, the choice of promoter and enhancer elements to be incorporated into a eukaryotic expression vector is determined by the cell type(s) in which the recombinant gene is to be expressed.

In one aspect, the regulatory elements of the invention may be heterologous with regard to each other or to a transgene, that is, they may be from different species. Furthermore, they may be from species other than the host, or they also may be derived from the same species but from different genes, or they may be derived from a single gene.

The present invention further encompasses kits.

Compositions of the present invention may be presented in a pack or dispenser device, such as an FDA approved kit, which may contain one or more unit dosage forms containing the therapeutic compound as described herein.

In some embodiments, the kit may include a therapeutic compound (as described herein), metal or plastic foil, such as a blister pack, a dispenser device or an applicator, tubes, buffers, and instructions for administration. The various reagent components of the kits may be present in separate containers, or some or all of them may be pre-combined into a reagent mixture in a single container, as desired. The dispenser device or applicator may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some cases, the kit includes at least one dose of monoclonal antibody (mAb) to CD24.

In some cases, the kit includes at least one dose of a fragment of monoclonal antibody (mAb) to CD24.

In some cases, the kit includes at least one dose of an expression vector comprising a nucleic acid sequence encoding the full length or segments of CD24 protein.

In some cases, the kit includes at least one dose of an expression vector comprising a nucleic acid sequence encoding the full length or segments of SCF protein.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out some embodiments of the present invention, and are not to be construed as limiting in any way the remainder of the disclosure. Therefore, the examples should be construed to encompass any and all variations which become evident as a result of the teaching provided herein.

EXAMPLES

Example 1

Administration of the anti-CD24 mAb induces stress erythropoiesis in mice, and expression of CD24 by cells of hematopoietic origin is required for induction of extra medullary hematopoiesis. Mice were infused intraperitoneally (i.p.) with 150 µg control rat IgG or αCD24 (clone M1/69) and necropsied on days 1, 3 or 5 after Ab treatment. (A) Representative macroscopic appearance of the spleens over time after αCD24 mAb infusion in wt B6 mice (n>20). Mice that received M1/69 exhibited marked splenomegaly first demonstrable at d3 post treatment. (B) M1/69 treatment promotes stress erythropoiesis. As mice and likely men typically respond to anemia and other hypoxic stresses by inducing extramedullary stress erythropoiesis in the spleen, we examined spleens of M1/69-treated mice in more detail. Single cell suspensions prepared from spleens at d5 post treatment were analyzed for cell types expressed by flow cytometry and enumerated (n≥5). Interestingly, this increase in spleen size cannot be attributed to leukocyte (CD45$^+$Ter119$^-$, group I) expansion, as leukocyte numbers were unaffected by M1/69-treatment (B) as well as the distribution of lymphocytic- and myeloid-lineage cells (data not shown). Therefore, we turned into examining the splenic erythroid compartment, based on the expression of the erythroid lineage cell surface marker Ter119. We found that the spleens of M1/69—treated mice have a dramatic increase in erythrocytes (CD45$^+$Ter119$^+$, group II) and erythroid progenitor cells (CD45$^-$Ter119$^+$, group III), respectively, with the most dramatic expansion observed within the spleen in the erythroid progenitor cell (CD45$^-$Ter119$^+$, group III) compartment. (C) We further examined for the erythroid compartment, based on the differential expression of Ter119 and the transferrin receptor, CD71. We found that the M1/69 treatment results in increase in all erythroblast subsets, consisting of basophilic (Ter119$^+$CD71$^{hi}$, group I—least mature), polychromatophilic (Ter119$^+$CD71$^{med}$, group ii), and orthochromatic (Ter119$^+$CD71$^{lo}$, group iii) erythroblasts in spleen. Of note, consistent with this notion, these erythroid progenitors underwent proliferation as determined by active uptake of BrdU and by staining for a proliferation-associated nuclear antigen, Ki-67 (data not shown). (D) Erythropoiesis induced by M1/69 treatment requires CD24 expression. To investigate if these effects are specific to M1/69 mAb interaction with CD24, mice deficient in CD24 expression were given Ig or αCD24 mAb and examined at d5 p.t. for gross appearance of spleens shown in (D) and absolute number of CD45$^-$Ter119$^+$ (data not shown, n=3-5). Therefore, M1/69 treatment did not have any off target effects (E) CD24 expression by the cells of hematopoietic origin, but not the cells in stromal compartment, is required for M1/69-induced stress erythropoiesis. CD24 (also known as heat stable antigen) is ubiquitously expressed on many cell types of hematopoietic (bone marrow-derived) and of non-hematopoietic origin. To assess the contribution of CD24-expressing cell type from the respective compartment, BM chimeric mice were established by transferring 2×10$^6$ donor BM cells derived from either WT or CD24$^{-/-}$ mice into lethally irradiated either WT or CD24$^{-/-}$ recipient mice. At 6 weeks after BM cell reconstitution, these chimeric mice were infused with Ig or M1/69. At d5, mice were necropsied and evaluated for gross appearance of spleens (right panel) and for erythroid progenitor cells frequency/numbers (left panel) (n=3/group). CD24 expression on cells of bone marrow/hematopoietic origin was necessary and sufficient for stress-induced hematopoiesis mediated by M1/69 treatment. It is also noteworthy that erythropoiesis induced by αCD24 mAb depends on F(ab)$_2$, but not Fc, fragments (data not shown). Data represent mean±SD. ***$P<0.001$.

Stress erythropoiesis in the peripheral blood after αCD24 mAb treatment. The effect of M1/69 treatment in erythropoiesis was also observed in peripheral blood. WT mice were infused i.p. with 150 µg control Ig or αCD24 and examined at the indicated time points. Peripheral blood smears were prepared at d5 p.t. and stained by methylene blue. Typical staining of residual RNA in reticulocytes—immature RBC for about a day in the blood stream before developing into mature RBCs—is examined by microscope (data now shown). (A) Percentages of reticulocytes in the peripheral blood were also assessed by flow cytometry using thiazole orange staining (to selectively stain nucleic acid, in this case RNA) for about an 1 hr at room temperature. A representative flow cytometric analysis of examining reticulocytes in blood at d5 is shown. Data are representative of >20 independently repeated experiments. Numbers denote the percentage of reticulocytes staining with thiazole orange dye in peripheral blood. (B) Kinetic analyses of percent reticulocytes circulating in the blood of mice treated with Ig or αCD24 at the indicated dates (n=4–7/day).

Stress erythropoiesis induced by αCD24 mAb treatment depends on the spleen and, to a lesser extent, bone marrow. Increased erythropoiesis is a key component of a physiological stress response to increase oxygen delivery to tissues. While earlier works have identified the murine spleen as the primary site of erythropoiesis in response to hypoxic conditions, stress erythropoiesis is also viewed as an intensified version of steady state erythropoiesis, which for the most part is restricted to the bone marrow. To study the extent of CD24-induced erythropoiesis in the spleen as well as BM, respectively, WT mice were injected i.p. with 150-µg control Ig or αCD24. (A) Representative of the frequency of CD45$^-$Ter119$^+$ erythroid progenitors in spleens (top panels in A) and BM (bottom panels in A), as measured by flow cytometry at d5 after αCD24 treatment. (B) Total erythroid progenitors per spleen and BM, respectively, at d5 are depicted (n=3-5). (C-E) To evaluate the impact of spleen on stress erythropoiesis, mice were splenectomized prior to antibody administration. WT B6 mice that had undergone splenectomy 5 weeks earlier were treated as in A. At d5, percentage of reticulocytes in the blood (C and D) and absolute cell number of CD45$^-$ Ter119$^+$ cells in BM (E) was assessed by flow cytometric analyses (n=3-5). Mean±SD is shown (*P<0.001, P<0.01 and **P<0.05). These data indicate that spleen is the major site for stress erythropoiesis induced by αCD24 mAb. However, while the bone marrow is a minor contributor to αCD24-induced erythropoiesis when the spleen is present, bone marrow displays a more vigorous stress erythropoiesis response in the absence of spleen, presumably as a compensatory mechanism.

Figure 1E:
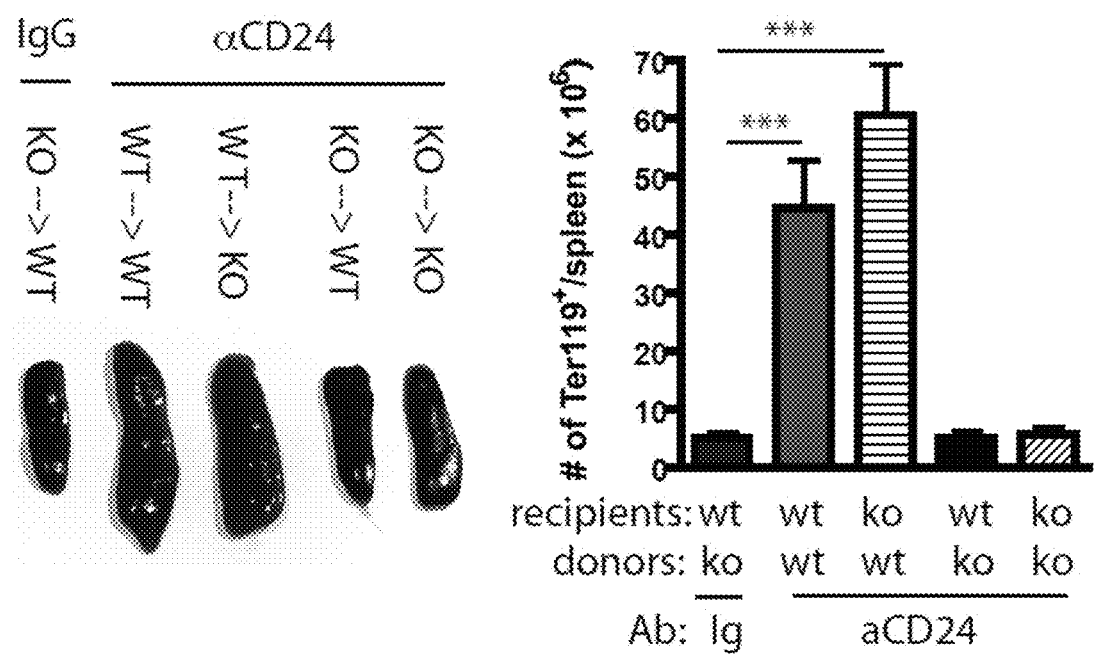

A novel role of conventional dendritic cells, in particular CD8α+ DC, in CD24-mediated stress erythropoiesis in vivo. Maintenance of the number of circulating RBCs is a tightly regulated process balancing between the production of RBCs derived from erythroid progenitors and the removal of the senescent RBCs by the hemophagocytic system. The cell types that are critically involved in regulating stress erythropoiesis in vivo are unclear. Our data shown in FIG. 1E indicate that cells originating from hematopoietic compartment are required for stress erythropoiesis induced by αCD24 mAb treatment. To investigate the specific cell type(s) governing stress erythropoiesis in vivo, we employed mice deficient in or depleted of various cell types (T, B, and inflammatory monocytes, neutrophils and NK cells) (See FIG. 4). Our analyses found that none of these hematopoietic cell lineages were important regulators of stress erythropoiesis induced by M1/69 treatment (data not shown). Next, we assessed the impact of dendritic cells (DCs) on the stress erythropoiesis. DCs are well recognized as professional antigen presenting cells, composed of heterogeneous subpopulations. In lymphoid organs such as spleens, three major subsets of DCs are classified; two conventional DC (cDC) subsets including CD8α$^+$CD11b$^-$ (CD8α$^+$ cDC, group I) and CD8α$^-$CD11b$^+$ (CD11b$^+$ cDC, group II) (top panels in A) and plasmacytoid DC (pDC) (data not shown). Notably, it is the CD8α$^+$ cDC among DC subsets in the spleen which express cell surface CD24 at the highest level (lower panel in A). To study the role of CD24$^{hi}$ CD8α$^+$ cDC in αCD24 mAb-induced stress erythropoiesis, we obtained mice lacking transcriptional factor Batf3 gene (Batf3 KO mice), which are developmentally devoid of CD8α$^+$ cDC in the spleen and of nodes and a related lineage of DC which populate certain non-lymphoid tissues such as lung and kidney etc. (B). WT and Batf3 KO mice were injected i.p. with 150 μg control Ig or αCD24. After 5 days, gross appearance of spleens (data not shown), a representative of the percentage of circulating reticulocytes in the blood (C) and absolute number of CD45$^-$Ter119$^+$ erythroid progenitors in the spleens (D) were assessed by flow cytometry (n=4-6). The results of these analyses indicate that CD8α$^+$ cDC in the spleen and possibly a related tissue-specific DC subset play a critical role in promoting stress erythropoiesis. To exclude a possibility of an additional unanticipated role of the Batf3 gene on erythropoiesis, i.e., other than its role in the generation of a specific DC lineage, we employed CD11c-DTR mice, which are engineered to express non-human primate diphtheria toxin receptor (DTR) driven off of murine CD11c (a conventional marker for murine DC) promoter. Upon diphtheria toxin (DTx) administration (100 ng/mouse via i.p.), DTR expressing CD11c$^+$ cells (that is cDC) are conditionally selectively ablated within 24 hrs (E). These cDC-ablated mice were infused with Ig or αCD24 mAb 1 day after first DTx administration. With second dose of DTx at d1 post treatment, mice were necropsied at d5 for gross appearance of the spleens (data not shown). The percentage of circulating reticulocytes in the blood (data not shown) and absolute number of CD45$^-$ Ter119$^+$ erythroid progenitors in the spleens (F) were assessed by flow cytometry (n=3-5). The analysis demonstrates that CD11c$^+$ cells, i.e., cDC, play a critical role in regulating the development of stress hematopoiesis mediated by CD 24 engagement. Data represent mean±SD.

Conventional DCs are required for the expansion of c-Kit expressing erythroid progenitors in the spleen during extramedullary stress erythropoiesis. Our data thus far are consistent with the prevailing view that the spleen is a major organ for extramedullary stress erythropoiesis and that this process can be triggered by engagement of CD24, and finally that cDC are essential for the physiological process of the extramedullary erythropoiesis in vivo. Recent studies show that stress erythropoiesis depends on a population of stress erythroid progenitor cells that are distinct from the counterpart present in BM. The development, expansion, and differentiation of these progenitors are regulated in part by a complex of less understood signals. We initially attempted to identify these progenitors based on c-Kit (CD117) expression as engagement of this receptor has been demonstrated to be essential for stress erythropoiesis. (FIG. 5 A-C) WT mice were injected i.p. with 150 μg control Ig or αCD24. (5A) Anti-CD24 mAb treatment promotes the expansion of cKit$^+$CD45$^{+/-}$ cells in the spleen. At d3 and 5 post treatments, single cells suspensions prepared from the necropsied spleens were stained with fluorochrome-conjugated mAb recognizing c-Kit (left panel). In contrast to Ig treated mice, mice undergoing M1/69 treatment have a dramatic increase in the number of c-Kit$^+$ cells, peaking at d3 (n>6), with little to no expression of the standard hematopoietic lineage marker CD45 (i.e., CD45$^{+/-}$c-Kit$^+$cells (right panel). (5B) CD45$^{+/-}$c-Kit$^+$ progenitors exhibited greater (compared to DC and B cells) forward (FSC) and side scatter (SSC) plot by flow cytometry analyses and expressed different levels of Ter119 as well as CD71, indicative of progenitor cells with erythroid lineage commitment such as proerythroblasts. (C) To determine if c-Kit$^+$ proerythroblasts undergo proliferative expansion, the M1/69-treated mice were fed with nucleic acid analog, BrdU, at d5 to label proliferating cells. After 24 hr BrdU injection, c-Kit$^+$ erythroid progenitors were examined for active uptake of BrdU in combination with staining for a proliferation-associated nuclear antigen, Ki-67. In contrast to c-Kit$^+$ cells in the Ig-treated spleen, c-Kit$^+$ erythroid progenitors isolated from the mice treated with M1/69 underwent active proliferation. (D) Furthermore, in support of the importance of splenic cDC in orchestrating stress erythropoiesis, ablation of cDC by treatment of CD11c-DTR mice with diphtheria toxin resulted in minimal expansion of these progenitors when stimulated by αCD24 mAb infusion (n=3-5). Collectively, our data strongly support the view that cDCs, particularly lymph node-resident CD8α+cDC subset and/or a developmentally related tissue-resident cDC subset, play an essential role in regulating extramedullary stress erythropoiesis.

Stem cell factor produced by cDC in the spleen is required for extramedullary stress erythropoiesis. We next investigated the molecular mechanism underlying cDC-dependent proerythroblast proliferation (FIG. 6). Soluble mediators—i.e., Erythropoietin (Epo), stem cell factor (SCF) and bone morphogenetic protein 4 (BMP 4), IL-3 and GM-CSF—have each been implicated as necessary to expand erythroid progenitors during erythropoiesis. We first examined the profile of gene expression by cDC and non-DC subpopulations after magnetically sorting out the cell types from total splenic cells prepared at d1 (data now shown) or d2 (A) or after M1/69 infusion. The splenic cells were sorted into DCs (based on CD11c$^+$), T cells (CD90$^+$), B cells (B220$^+$) and remaining cell types, i.e., both CD45$^+$ hematopoietic origin cells and CD45$^-$ splenic stromal cells. We measured expression levels of mRNA encoding for SCF, Epo, BMP4, IL-3, and GM-CSF, respectively. Our data revealed that M1/69 treatment induced the expression of SCF exclusively by cDC (6A). In contrast, cDC in the spleen did not upregulate mRNA for Epo, BMP4, IL-3 and GM-CSF (data now shown). (6B-D) This suggests that SCF produced by splenic cDC via CD24 signaling contributes to M1/69-induced erythropoiesis. To investigate the role of SCF-c-Kit signaling in stress erythropoiesis, c-Kit KO mice were infused with αCD24 mAb. c-Kit deficiency resulted in an a markedly reduced percentage of reticulocytes in peripheral blood of mAb treated KO mice compared to treated wild type control mice when analyzed at d5 after mAb infusion (B). The importance of c-kit-mediated signaling in this process was further validated by the analysis of the gross appearance of spleens (C) and the accumulation of c-Kit$^-$ erythroid progenitors (CD45$^-$Ter119$^+$, left panel in D) and c-Kit$^+$ proerythroblasts (right panel in D) in the spleens at d5 after mAb infusion. As shown in C and D, the absence of c-Kit-SCF signaling axis resulted in the almost complete abrogation of M1/69-stimulated erythropoiesis. (6E and F) We complemented the findings in c-Kit KO mice on the extramedullary stress erythropoiesis, by analyzing the impact of the pharmacological inhibitor of c-Kit signaling, imatinib (Gleevec). The drug (1 mg/kg) was administrated i.p. daily for 4 days into M1/69-treated WT mice. Consistent with the observations in c-Kit KO mice, administration of Imatinib into mAb treated WT B6 mice significantly reduced the reticulocytes in the blood (E) and inhibited the expansion/accumulation of CD45$^-$ Ter119$^+$ erythroid progenitors (left panel in F) and c-Kit$^+$ proerythroblasts (right panel in F) in the spleen. In summary, our data suggest that SCF produced by splenic cDC stimulated by engagement of the CD24 molecule on the cells with the M1/69 mAb promotes the expansion of c-Kit+ erythroid progenitors in the spleen through a engagement of the c-Kit receptor on the early splenic erythroid progenitors.

FIG. 7. Stress erythropoiesis triggered by M1/69 treatment requires Epo production by the kidneys, and Epo production is in turn dependent on the presence of cDC. Epo is a glycoprotein hormone that serves as a primary regulator of differentiation, proliferation, and survival of erythroid progenitor cells, and is made mainly by stromal cells within the kidneys. Epo and c-Kit signaling are both necessary for efficient erythropoiesis and work synergistically in this process. To fully account for the robust expansion of erythroid lineage progenitor cells in the spleen and the subsequent reticulocytosis following mAb treatment, we postulated that engagement of CD24 stimulates directly or indirectly Epo production by stromal cells in the kidney, which acts in concert with SCF produced locally in spleen to orchestrate extramedullary hematopoiesis. (FIG. 7A) When serum Epo levels were measured after M1/69 injection, we indeed detected a robust increase in Epo, peaking d3 after injection and then gradually decreasing over the several days. This burst of Epo production, as expected, proceeds the appearance of reticulocytes in the peripheral blood (see FIG. 2). (7B) In FIG. 6, we demonstrated that cDCs are critical in stress erythropoiesis induced by M1/69 treatment at least via the provision of SCF to stimulate the expansion of c-Kit receptor-expressing erythroid progenitors in the spleen. We reasoned that in parallel to splenic cDC, the counterpart of cDC subsets in the kidney may play a crucial role in promoting the production of Epo by epo-producing renal stromal cells. To test this hypothesis, we first measured Epo levels in the circulation of mice deficient in cDC, either genetically (i.e., Batf3 KO mice) or following cDC ablation (i.e., DTx-treated CD11c-DTR mice). We found a significant decrease in Epo production in Batf3 KO mice (7C) and nearly complete ablation of Epo production in DTx-treated CD11c-DTR mice (7D). These data demonstrate that cDCs localized in respective tissues play a crucial role in CD24-mediated stress erythropoiesis via at least stimulation of Epo induction in the kidneys and SCF production in the spleen. To dissect the contribution of Epo and SCF, respectively, we measured Epo concentration in c-Kit KO mice, which have an intact cDC compartment in the kidney (data not shown). In stark contrast to the absence of the expansion of c-Kit+ erythroid progenitors in the spleen, M1/69 treated c-Kit KO mice have demonstrated an elevated Epo level in the circulation. This is in keeping with the failure of expansion of c-Kit+ erythroid progenitors in the spleens of c-Kit KO mice which would be the primary consumers of Epo through binding of Epo to its receptor on the cells. This result indicates that the production of Epo alone, although necessary, is not sufficient to induce extramedullary stress erythropoiesis after CD24 engagement.

Model for CD24-mediated stress erythropoiesis in vivo. Without wishing to be bound by any particular theory, hypothesized herein is a novel model for extramedullary stress erythropoiesis in vivo after M1/69 treatment (FIG. 8). As described above, the present application discloses a previously unknown function of CD24 expressed by a distinct subset of splenic DCs; that is, engagement of CD24 on this spleen resident cell type stimulates EPO production and concomitant vigorous production of RBCs in the spleen and bone marrow. The current invention encompasses a novel strategy to enhance stress-mediated erythropoiesis. Hypoxic stresses such as anemia, blood loss, aging and so on release host-derived danger associated-pattern molecules (i.e., HMGB1, Hsp70, etc.), which are recognized by the CD24 receptor expressed on DCs residing in spleen and kidney, respectively. Ligation of CD24 on splenic DCs transduces intracellular signals to produce SCF, which act on neighboring c-Kit$^+$ progenitors with potential to commit toward erythroid lineage to undergo expansion. Concomitantly, CD24 interaction on DCs in the kidney results in stimulating in trans renal epithelial and/or tubular cells to produce growth factors, including mainly Epo and possibly BMP4. The proliferating proerythroblasts and erythroid progenitor cells in the spleen receive the second signals through Epo receptors and undergo further differentiation, proliferation, and maturation in the spleen, ultimately releasing reticulocytes into the circulation to deliver oxygen.

Example 2

The present example provides: 1.) analysis in the mouse of erythropoiesis following administration of other monoclonal antibodies to CD24; 2.) an analysis of the reticulocyte response following a second administration of the CD24 agonistic mAb; and 3.) an analysis of the response of the human DC subset corresponding to the murine CD8α$^+$ DC subset found in the murine spleen to stimulation by human anti-CD24 mAbs on the expression of human SCF.

I. Along with the prototype M1/69 mAb to CD24 employed in Example 1, the present example includes the analysis of the stimulation of splenic erythrocyte progenitor (Ter119$^+$CD45$^-$ cells) expansion in the spleen following administration of M1/69 or 1 of 3 other monoclonal anti-CD24 antibodies, 91, 30-F 1, and J11 d, respectively. These data are included in Supplemental FIGS. 1A and 1B. The results demonstrate that M1/69 and 91 are potent stimulators of erythropoiesis while 30-F1 antibody has an immediate potency and the J11d has a weak or no activity.

II. Supplemental FIG. 2 shows the results of an analysis of the reticulocyte response to repeated administration of monoclonal antibody. In this instance, mice were first injected with M1/69 and the reticulocyte count in the blood was evaluated over time. At day 8 after the injection of the M1/69 antibody, the mice received either a second injection of M1/69 antibody or an injection of 1 of the 3 additional anti-CD24 monoclonal antibodies and the reticulocyte response to a second exposure to anti-CD24 antibody was monitored over time. The 3 monoclonal antibodies with stimulatory capacity in primary treatment (i.e., M1/69, 91 and 30-F 1) could each stimulate a second wave of reticulocytosis.

III. In Supplemental FIG. 3 we have isolated conventional dendritic cells from the spleens of mice in the usual fashion and were treated with anti-CD24 monoclonal antibody overnight in cultures. We monitored the expression of the murine stem cell factor (mSCF) on the splenic $CD8\alpha^+$ DC subset and the more abundant $CD8\alpha^-$ $CD11b^+$ splenic DCs. As the figure indicates, mSCF is abundantly expressed on the surface of $CD8\alpha^+$ DC subset.

The human dendritic cell subset corresponding to the murine $CD8\alpha^+$ DC expresses the cell surface molecule BDCA3 (CD141) and is present in the human spleen. Therefore, in humans, the primary targeted DC cell subset are those cells expressing the cell surface molecule BDCA3 (CD141).

Human spleen will be tested as described above for mouse cells. We're currently in the process of obtaining human spleen for the isolation of this DC subset and for the analysis of the impact of stimulation of CD24 displayed by these dendritic cells on the up-regulation of expression of human stem cell factor (hSCF) on the surface of the cells.

IV. In the interim we have employed a strategy for generating $BDCA3^+$ DC from human peripheral blood mononuclear cells in vitro using a cocktail of growth factors consisting of GM-CSF, IL-4, SCF, and Flt3L. This cocktail can also be used in conjunction with the other agents of the invention to stimulate erythropoiesis in a subject in need thereof. These growth factors are highly potent stimulators of proliferation and differentiation of circulating mononuclear stem cells into a variety of cell types. Nonetheless, as Supplemental FIG. 4A demonstrates we can detect a small population of $BDCA3^+$ DC-like cells in in vitro culture with a larger population of $BDCA3^-$ cells. As Supplemental FIG. 4B demonstrates we can detect up-regulation of hSCF in response to treatment with 2 different monoclonal antibodies to human CD24: eBioSN3 and MLS.

As demonstrated in Supplemental FIG. 4 B, the BioSN3 monoclonal antibody regulates hSCF expression selectively on $BDCA3^+$ DC. Note that the background expression of cell surface hSCF is high in both DC subsets. This may be due to the strong growth promoting activity of the growth factor cocktails. When this analysis is repeated with resting $BDCA3^+$ DC isolated from human spleen, the background might be lower. Nevertheless, these findings demonstrate that the corresponding up-regulation of cell surface hSCF by engagement of the CD24 receptor occurs as well in the corresponding population of human dendritic cells.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Hunte B E, Capone M, Zlotnik A, Rennick D, Moore T A. 1998. Acquisition of CD24 expression by Lin-CD43+ B220(low)ckit(hi) cells coincides with commitment to the B cell lineage. Eur J Immunol. 28(11):3850-6.
2. Wilson, A., L. M. Day, et al. 1988. Subpopulations of mature murine thymocytes: properties of CD4−CD8+ and CD4+CD8− thymocytes lacking the heat-stable antigen. Cell Immunol 117(2): 312-26.
3. Alterman, L. A., I. N. Crispe, et al. 1990. Characterization of the murine heat-stable antigen: an hematolymphoid differentiation antigen defined by the J11d, M1/69 and B2A2 antibodies. Eur J Immunol 20(7): 1597-602.
4. Springer T, Galfre G, Secher D S, Milstein C. 1978. Monoclonal xenogeneic antibodies to murine cell surface antigens: identification of novel leukocyte differentiation antigens. Eur J Immunol. 8(8):539-51.
5. Thomas et al., epub. Aug. 27, 2012, Cancer Research, CD24 is an effector of HIF-1 driven primary tumor growth and metastasis.
6. Zhou, Q., et al., "CD24 is a genetic modifier for risk and progression of multiple sclerosis", PNAS, 2003, Vol. 100, No. 25, 15041-15046.
7. Jaggupilli, A., et al., "Significance of CD44 and CD24 as Cancer Stem Cell Markers: an Enduring Ambiguity", Clinical and Developmental Immunology", Vol. 2012, Article ID 708036, 1-11.
8. Fischer, G., et al., "Signal Transcution in Lymphocytic and Myeloid Cells via CDE 24, A New Member of Phosphoinositol-Anchored Membrane Molecules[1]". Journal of Immunology, Vol. 144, No. 2, 1990, 638-641.
9. Wu, D., et al., "Antibody-Directed Lentiviral Gene Transduction for Live-Cell Monitoring and Selection of Human iPS and hES Cells", PLos ONE, April, 2012, Vol. 7, Issue 4, 1-10.
10. Kume, A., et al., "Long-term tracking of murine hematopoietic cells transduced with a bicistronic retrovirus containing CD24 and EGFP genes", Gene Therapy (2000), 7, 1193-1199.
11. Cao, X., et al., "Upregulation of VEGF-A and CD24 Gene Expression by the tGLI1 Transcription Factor Contributes to the Aggressive Behavior or Breast Cancer Cells", Oncogene, January, 2012, 31 (1): 104-115.
12. Williams, L., et al., "Identification of a novel dendritic cell surface antigen defined by carbohydrate specific CD24 antibody cross-reactivity", Immunology 1996, 89, 120-125.

13. Zhu, J., et al., "Identification of Glycoprotein Markers for Pancreatic Cancer CD24+CD44+ Stem-like Cells Using Nano-LC-MS/MS and Tissue Microarray", J. Proteome Research 2012, 11, 2272-2281.
14. Fang, X., et al., "CD24: from A to Z", Cellular & Molecular Immunology" (2010), 7, 100-103.
15. Kay, F., et al., "CD24, A Signal Transducer Modulating B Cell Activation Responses, is a Very Short Peptide with a Glycosyl Phosphatidylinositol Membrane Anchor[1]", J. of Immunology, Vol. 147, 1412-1416, No. 4, Aug. 15, 1991.
16. Salamone, M., et al., "Antibodies recognizing CD24 LAP epitope on human T cells enhance CD28 and IL-2 T cell proliferation", J. of Leukocyte Biology, Vol. 69, February 2001, 215-223.

What is claimed is:

1. A method of stimulating CD24 expressed on dendritic cells and stimulating erythropoiesis in a subject in need thereof, said method comprising administering to said subject a pharmaceutical composition comprising a pharmaceutically-acceptable carrier and an effective amount of an agonist of said CD24, wherein said agonist is an antibody directed against a CD24 peptide having the amino acid sequence of SEQ ID NO:2 or SEQ ID NO:4, wherein said antibody is a monoclonal antibody selected from the group consisting of M1/69, 91, 30-F1, eBioSN3, and ML5, and F(ab)$_2$ fragments thereof; and wherein said agonist binds CD24 on dendritic cells and stimulates CD24 expressed on said dendritic cells, thereby stimulating erythropoiesis in said subject, wherein said subject has a disease, disorder or condition associated with a decrease in erythrocyte product selected from the group consisting of anemia, chronic renal failure, end-stage renal disease, acquired immune deficiency syndrome, chemotherapy, radiotherapy, sepsis, and chronic persistent infection.

2. The method of claim 1, wherein said pharmaceutical composition comprises at least one additional therapeutic agent.

3. The method of claim 2, wherein said method stimulates dendritic cells.

4. The method of claim 1, wherein said dendritic cells express the cell surface molecule BDCA3/CD141.

5. The method of claim 1, wherein said method stimulates the production of erythrocytes.

6. The method of claim 1, wherein said method stimulates the production of reticulocytes.

7. The method of claim 1, wherein said method stimulates the production of erythroid progenitor cells.

8. The method of claim 1, wherein said dendritic cells are in the spleen.

9. The method of claim 1, wherein said dendritic cells are in the bone marrow.

10. The method of claim 1, wherein said method stimulates erythropoietin production.

11. The method of claim 1, wherein said method stimulates extramedullary hematopoiesis.

12. The method of claim 1, wherein said method increases levels of stem cell factor (SCF), granulocyte colony stimulating factor (G-CSF), and erythropoietin (EPO).

13. The method of claim 1, wherein said method enhances CD24-mediated stress erythropoiesis.

14. The method of claim 1, wherein said method stimulates proliferation of erythroid progenitor cells.

15. The method of claim 1, wherein the subject has anemia, and wherein said anemia is selected from the group consisting of aplastic anemia, hypoplastic anemia, and chronic anemia in the elderly.

16. The method of claim 1, wherein the subject has anemia.

17. The method of claim 16, wherein said anemia is associated with hypoxic stress.

18. The method of claim 1, wherein said pharmaceutical composition comprises an additional therapeutic agent, wherein said additional therapeutic agent is selected from the group consisting of G-CSF, interleukin-4 (IL-4), SCF, Fms-Like Tyrosine Kinase 3 Ligand (Flt3L), EPO, bone morphogenic protein 4 (BMP4), anti-microbial agents, and host-derived danger associated-pattern molecules.

19. The method of claim 18, wherein said host-derived danger associated-pattern molecule is high mobility group protein group B1 (HMGB1) or Hsp70.

20. The method of claim 1, wherein said pharmaceutical composition is administered at least twice.

21. The method of claim 20, wherein said pharmaceutical composition is administered at least five times.

22. The method of claim 21, wherein said pharmaceutical composition is administered at least 10 times.

23. The method of claim 1, wherein said pharmaceutical composition is administered at least once per day.

24. The method of claim 23, wherein said pharmaceutical composition is administered at least once per week.

25. The method of claim 24, wherein said pharmaceutical composition is administered at least twice per week.

26. The method of claim 23, wherein said pharmaceutical composition is administered at least once per month.

27. The method of claim 26, wherein said pharmaceutical composition is administered at least twice per month.

28. The method of claim 1, wherein said method increases erythrocyte levels.

29. The method of claim 1, wherein said antibody is administered at a dose ranging from about 0.1 mg/kg to about 25.0 mg/kg body weight.

30. The method of claim 29, wherein said antibody is administered at a dose ranging from about 1.0 mg/kg to about 15.0 mg/kg body weight.

31. The method of claim 30, wherein said antibody is administered at a dose ranging from about 5.0 mg/kg to about 10.0 mg/kg body weight.

32. The method of claim 1, wherein said subject is human.

* * * * *

SEQUENCE LISTING

<160> NUMBER OF SEQ ID NOS: 4

<210> SEQ ID NO 1
<211> LENGTH: 2194
<212> TYPE: DNA
<213> ORGANISM: Homo sapiens

<400> SEQUENCE: 1

```
gggtctcgcc ggctcgccgc gctccccacc ttgcctgcgc ccgcccggag ccagcggttc      60
tccaagcacc cagcatcctg ctagacgcgc cgcgcaccga cggaggggac atgggcagag     120
caatggtggc caggctcggg ctggggctgc tgctgctggc actgctccta cccacgcaga     180
tttattccag tgaaacaaca actggaactt caagtaactc ctcccagagt acttccaact     240
ctgggttggc cccaaatcca actaatgcca ccaccaaggc ggctggtggt gccctgcagt     300
caacagccag tctcttcgtg gtctcactct ctcttctgca tctctactct taagagactc     360
aggccaagaa acgtcttcta aatttcccca tcttctaaac ccaatccaaa tggcgtctgg     420
aagtccaatg tggcaaggaa aaacaggtct tcatcgaatc tactaattcc acacctttta     480
ttgacacaga aaatgttgag aatcccaaat ttgattgatt tgaagaacat gtgagaggtt     540
tgactagatg atggatgcca atattaaatc tgctggagtt tcatgtacaa gatgaaggag     600
aggcaacatc caaaatagtt aagacatgat ttccttgaat gtggcttgag aaatatggac     660
acttaatact acccttgaaaa taagaataga aataaaggat gggattgtgg aatggagatt     720
cagttttcat ttggttcatt aattctataa ggccataaaa caggtaatat aaaaagcttc     780
catgattcta tttatatgta catgagaagg aacttccagg tgttactgta attcctcaac     840
gtattgtttc gacagcacta atttaatgcc gatatactct agatgaagtt ttacattgtt     900
gagctattgc tgttctcttg ggaactgaac tcactttcct cctgaggctt tggatttgac     960
attgcatttg acctttttatg tagtaattga catgtgccag ggcaatgatg aatgagaatc    1020 taccccccaga tccaagcatc ctgagcaact cttgattatc catattgagt caaatggtag    1080
gcatttccta tcacctgttt ccattcaaca agagcactac attcatttag ctaaacggat    1140
tccaaagagt agaattgcat tgaccacgac taatttcaaa atgcttttta ttattattat    1200
tttttagaca gtctcacttt gtcgcccagg ccggagtgca gtggtgcgat ctcagatcag    1260
tgtaccattt gcctcccggg ctcaagcgat tctcctgcct cagcctccca agtagctggg    1320
attacaggca cctgccacca tgcccggcta attttttgtaa ttttagtaga cagggtttt    1380 caccatgttg cccaggctgg tttcgaactc ctgacctcag gtgatccacc cgcctcggcc    1440
tcccaaagtg ctgggattac aggcttgagc ccccgcgccc agccatcaaa atgcttttta    1500
tttctgcata tgttgaatac ttttttacaat ttaaaaaaat gatctgtttt gaaggcaaaa    1560
ttgcaaatct tgaaattaag aaggcaaaaa tgtaaggag tcaaaactat aaatcaagta    1620
tttgggaagt gaagactgga agctaatttg cattaaattc acaaactttt atactctttc    1680
tgtatataca ttttttttct ttaaaaaaca actatggatc agaatagcca catttagaac    1740
```

```
actttttgtt atcagtcaat attttagat agttagaacc tggtcctaag cctaaaagtg    1800
ggcttgattc tgcagtaaat cttttacaac tgcctcgaca cacataaacc tttttaaaaa    1860
tagacactcc ccgaagtctt tgttcgcat ggtcacacac tgatgcttag atgttccagt    1920
aatctaatat ggccacagta gtcttgatga ccaaagtcct ttttttccat ctttagaaaa    1980
ctacatggga acaaacagat cgaacagttt tgaagctact gtgtgtgtga atgaacactc    2040
ttgctttatt ccagaatgct gtacatctat tttggattgt atattgtgtt tgtgtattta    2100
cgctttgatt catagtaact tcttatggaa ttgatttgca ttgaacacaa actgtaaata    2160
aaaagaaatg gctgaaagag caaaaaaaaa aaaa    2194
```

<210> SEQ ID NO 2
<211> LENGTH: 80
<212> TYPE: PRT
<213> ORGANISM: Homo sapiens

<400> SEQUENCE: 2

```
Met Gly Arg Ala Met Val Ala Arg Leu Gly Leu Gly Leu Leu Leu Leu
 1               5                  10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80
```

<210> SEQ ID NO 3
<211> LENGTH: 1825
<212> TYPE: DNA
<213> ORGANISM: Mus musculus

<400> SEQUENCE: 3

```
ccaccttgcc tgcgcccgcg cgagcttagc agatctccac ttaccgaaca tctagagagt      60
cgcgccgcgc gccgacggag cggacatggg cagagcgatg gtggccaggc tagggctggg     120
gttgctgctt ctggcactgc tcctacccac gcagatttac tgcaaccaaa catctgttgc     180
accgtttccc ggtaaccaga atatttctgc ttccccaaat ccagtaacg ctaccaccag      240 agggggtggc agctccctgc agtccacagc tggtctcctg gctctctctc tctctcttct     300
acatctctac tgttagagac tcaggccagg aaacgtctct acttcccat cttctacacc      360 taccccaaat ggcaaccaca agtccaatgt gatcaggaag aaacaggtcc acctcgaatt     420
ggctgttacc atatctcaac agaaaacacg gagaattcga attcgacgg gattaaagga      480 cgcgtgaaag gtttgagaga agagagatgc cgctattgaa tctgctggag ttttacatcc     540
caagatgaag acagcattca gaattgatgt gatttccttg aatgtggctt aggaaatgtg     600
gacacttaaa actctcactt gaaattgggc acaggtttga tgtagagata aggacggggt     660
gcggaatgga gacccatttt gtcattgatt catctgaccg ataaggccat agtgcagtta     720
ggtgatattc gaaagcttct tgatgctct ttatgtatat gttggaagga actaccaggc      780
gttgctttaa attcccaatg tgttgtttcg ttactactaa tttaatacgg taagctctag      840
gtaaagttcc atgttgttga actctgactg ttctctttgg aattgaacgt ttgcatcct      900 cctcctgtgg ctttaggtct gacattgtat ttgaccttta ctagtaatta acatgtgcca     960
```

```
ggcaatggtg gattggaacc catccccaag tccagccacc actgaataaa tctgatttca   1020
aaagtcaaac agtagacatt tcccattgtc gtttctcact caccacaagc accaaattca   1080
ctagagtaca ctggttccag agagcagaat catgttggcc ttggctaatt tcaaaatgct   1140
gtcttttact ttggtatatg ttgagggctt ttcataattt aaagtgtgtt ctgttagcaa   1200
ggcaaaaatt atgagtctta attctacagg caaatatgca aaggagccaa aactgtaaac   1260
ccagcatttg ggatgtgaag actggaagct aactctcatt gaattcacaa agtcttttat   1320
acaatttctg tacatacttt tttttttttt aagagaaaaa caaacggtgg atcagaatag   1380
ccacgtttgg aatactttgg ttatccattc atatttttag atagttattg gtcctgtgcc   1440
tgaaaggggg cttggttcta ccgtaagttt ttccaatttc cttgatatac atataccttc   1500
taaaacctag acatttcctg aaaaaaatct tttgttcgca tggtcacaca ctgatgctta   1560
cccgtacagt agtcttgata accagagtca ttttctccat ctttagaaac cttcctggga   1620
agaaggagag ctcacagacc cgaagctact gtgtgtgtga atgaacactc cccttgcctc   1680
acacctgaat gctgtacatc tatttgattg taaattgtgt ttgtgtattt atgctttgat   1740
tcatagtaac ttctcatgtt atggaattga tttgcattga acacaaactg taaataaaag   1800
aaagaaatgg cggagaaaaa aaaaa                                         1825

<210> SEQ ID NO 4
<211> LENGTH: 76
<212> TYPE: PRT
<213> ORGANISM: Mus musculus

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Cys Asn Gln Thr Ser Val Ala
            20                  25                  30

Pro Phe Pro Gly Asn Gln Asn Ile Ser Ala Ser Pro Asn Pro Ser Asn
        35                  40                  45

Ala Thr Thr Arg Gly Gly Gly Ser Ser Leu Gln Ser Thr Ala Gly Leu
    50                  55                  60

Leu Ala Leu Ser Leu Ser Leu Leu His Leu Tyr Cys
65                  70                  75
```